United States Patent
Yousefi et al.

(10) Patent No.: US 11,063,637 B2
(45) Date of Patent: Jul. 13, 2021

(54) SYSTEMS AND METHODS FOR LOW-POWER NEAR-FIELD-COMMUNICATION

(71) Applicant: The Regents of the University of California, Oakland, CA (US)

(72) Inventors: Alireza Yousefi, Corona, CA (US); Asad A. Abidi, Los Angeles, CA (US); Dejan Markovic, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/611,821

(22) PCT Filed: May 9, 2018

(86) PCT No.: PCT/US2018/031902
§ 371 (c)(1),
(2) Date: Nov. 7, 2019

(87) PCT Pub. No.: WO2018/208990
PCT Pub. Date: Nov. 15, 2018

(65) Prior Publication Data
US 2020/0186201 A1    Jun. 11, 2020

Related U.S. Application Data

(60) Provisional application No. 62/503,846, filed on May 9, 2017, provisional application No. 62/666,460, filed on May 3, 2018.

(51) Int. Cl.
*H04B 5/00* (2006.01)
*G04F 10/00* (2006.01)
*H03L 7/093* (2006.01)

(52) U.S. Cl.
CPC ......... *H04B 5/0075* (2013.01); *G04F 10/005* (2013.01); *H03L 7/093* (2013.01); *H04B 5/0031* (2013.01); *H04B 5/0037* (2013.01)

(58) Field of Classification Search
CPC .................................................. H04B 5/0075
See application file for complete search history.

(56) References Cited

U.S. PATENT DOCUMENTS 4,561,443 A * 12/1985 Hogrefe ............... A61N 1/3727
128/903
4,654,880 A * 3/1987 Sontag .................... H04B 5/02
455/121
(Continued)

FOREIGN PATENT DOCUMENTS

WO    2018208990 A1    11/2018
WO    2019036519 A1    2/2019

OTHER PUBLICATIONS

International Preliminary Report on Patentability for International Application No. PCT/US2018/031902, Report dated Nov. 12, 2019, dated Nov. 21, 2019, 9 Pgs.
(Continued)

*Primary Examiner* — Hsinchun Liao
(74) *Attorney, Agent, or Firm* — KPPB LLP

(57) ABSTRACT

Systems and methods for using near-field inductive coupling between an implanted system and an external transceiver are discloses. In several embodiments, the data link system is based on a free-running oscillator tuned by coupled resonators. The use of an oscillator-based power link can allow for stable power over different inductor distances, or coil distances. In some embodiments, the data link system includes receivers on both sides of the link, where each receiver is
(Continued)

composed of a detector, such as but not limited to an analog front-end ("AFE"), and a clock and data recovery ("CDR") loop.

28 Claims, 24 Drawing Sheets

(56) References Cited

U.S. PATENT DOCUMENTS

| | | | |
|---|---|---|---|
| 2002/0032471 | A1 | 3/2002 | Loftin et al. |
| 2007/0132522 | A1* | 6/2007 | Lee ............... H03B 5/1265 331/167 |
| 2007/0210842 | A1* | 9/2007 | Kawamoto ........ H03L 7/0812 327/158 |
| 2010/0039092 | A1* | 2/2010 | Cordier ............ H01F 27/38 323/355 |
| 2010/0164458 | A1 | 7/2010 | Pollard |
| 2012/0071089 | A1 | 3/2012 | Charrat et al. |
| 2014/0015327 | A1 | 1/2014 | Keeling et al. |
| 2014/0273835 | A1 | 9/2014 | Ghovanloo et al. |
| 2015/0318932 | A1* | 11/2015 | Kerselaers ............ H04B 5/02 381/315 |
| 2016/0036244 | A1 | 2/2016 | Griffith |
| 2016/0149440 | A1 | 5/2016 | Staring et al. |
| 2017/0118543 | A1 | 4/2017 | Ha et al. |
| 2020/0220392 | A1 | 7/2020 | Pan et al. |

OTHER PUBLICATIONS

International Preliminary Report on Patentability for International Application PCT/US2018/046779, Report dated Feb. 18, 2020, dated Feb. 27, 2020, 5 Pgs.

International Search Report and Written Opinion for International Application No. PCT/US2018/031902, Search completed Jul. 5, 2018, dated Jul. 26, 2018, 15 Pgs.

International Search Report and Written Opinion for International Application No. PCT/US2018/046779, Search completed Oct. 11, 2018, dated Oct. 26, 2018, 11 Pgs.

Afshar et al., "A translational platform for prototyping closed-loop neuromodulation systems", Frontiers in Neural Circuits, Jan. 22, 2013, vol. 6, Article 117, 15 pgs., https://doi.org/10.3389/fncir.2012.00117.

Ahn et al., "Wireless Power Transmission With Self-Regulated Output Voltage for Biomedical Implant", IEEE Transactions on Industrial Electronics, vol. 61, Issue 5, May 2014, pp. 2225-2235.

Alexander, "Clock recovery from random binary signals", Electronics Letters, Oct. 30, 1975, vol. 11, No. 22, pp. 541-542, DOI: 10.1049/el:19750415.

Bihr et al., "Telemetry for implantable medical devices: Part 3—Data telemetry", IEEE Solid-State Circuits Magazine, Fall 2014, vol. 6, No. 4, pp. 56-62, DOI: 10.1109/MSSC.2014.2347812.

Bohorquez et al., "A 350 μW CMOS MSK Transmitter and 400 μW OOK Super-Regenerative Receiver for Medical Implant Communications", IEEE Journal of Solid-State Circuits, Apr. 2009, vol. 44, No. 4, pp. 1248-1259, DOI: 10.1109/JSSC.2009.2014728.

Ghovanloo et al., "A wideband frequency-shift keying wireless link for inductively powered biomedical implants", IEEE Transactions on Circuits and Systems I: Regular Papers, vol. 51, Issue 12, Dec. 2004, pp. 2374-2383.

Gibson et al., "Spike Sorting: The First Step in Decoding the Brain", IEEE Signal Processing Magazine, Jan. 2012, vol. 29, No. 1, pp. 124-143, DOI: 10.1109/MSP.2011.941880.

Ha et al., "Energy Recycling Telemetry IC With Simultaneous 11.5 mW Power and 6.78 Mb/s Backward Data Delivery Over a Single 13.56 MHz Inductive Link", IEEE Journal of Solid-State Circuits, vol. 51, Issue 11, Nov. 2016, pp. 2664-2678.

Hajimiri et al., "Design issues in CMOS differential LC oscillators", IEEE Journal of Solid-State Circuits, May 1999, vol. 34, No. 5, pp. 717-724, DOI: 10.1109/4.760384.

Hegazi et al., "A Filtering Technique to Lower LC Oscillator Phase Noise", IEEE Journal of Solid-State Circuits, vol. 36, Issue 12, Dec. 2001, pp. 1921-1930.

Hu et al., "A fully integrated low-power BPSK demodulator for implantable medical devices", IEEE Transactions on Circuits and Systems I: Regular Papers, Dec. 2005, vol. 52, No. 12, pp. 2552-2562, DOI: 10.1109/TCSI.2005.858163.

Huang et al., "A Wireless Power Transfer System with Enhanced Response and Efficiency by Fully-Integrated Fast-Tracking Wireless Constant-Idle-Time Control for Implants", Symposium on VLSI Circuits Digest of Technical Papers, Honolulu, Hawaii, Jun. 15-17, 2016, 2 pgs.

Inanlou, et al., "A 10.2 Mbps Pulse Harmonic Modulation Based Transceiver for Implantable Medical Devices", IEEE Journal of Solid-State Circuits, vol. 46, Issue 6, Jun. 2011, pp. 1296-1306.

Inanlou, et al., "Wideband Near-Field Data Transmission Using Pulse Harmonic Modulation", IEEE Transactions on Circuits and Systems I: Regular Papers, vol. 58, Issue 1, Jan. 2011, pp. 186-195.

Jiang et al., "An Integrated Passive Phase-Shift Keying Modulator for Biomedical Implants With Power Telemetry Over a Single Inductive Link", IEEE Transactions on Biomedical Circuits and Systems, Feb. 2017, vol. 11, No. 1, pp. 64-77, DOI: 10.1109/TBCAS.2016.2580513.

Kiani et al., "A 13.56-Mbps Pulse Delay Modulation Based Transceiver for Simultaneous Near-Field Data and Power Transmission", IEEE Transactions on Biomedical Circuits and Systems, vol. 9, Issue 1, Feb. 2015, pp. 1-11.

Kiani et al., "A 20-Mb/s Pulse Harmonic Modulation Transceiver for Wideband Near-Field Data Transmission", IEEE Transactions on Circuits and Systems II: Express Briefs, vol. 60, Issue 7, Jul. 2013, pp. 382-386.

Kiani et al., "A power-management ASIC with Q-modulation capability for efficient inductive power transmission", ISSCC, 2015, pp. 226-227.

Kim et al., "Review of Near-Field Wireless Power and Communication for Biomedical Applications", IEEE Access, Sep. 27, 2017, vol. 5, pp. 21264-21285, DOI: 10.1109/ACCESS.2017.2757267.

Kuan et al., "Wireless Gigabit Data Telemetry for Large-Scale Neural Recording", IEEE Journal of Biomedical and Health Informatics, May 2015, vol. 19, No. 3, pp. 949-957, DOI: 10.1109/JBHI.2015.2416202.

Li et al., "Wireless Power Transfer System Using Primary Equalizer for Coupling- and Load-Range Extension in Bio-Implant Applications", IEEE International Solid-State Circuits Conference—(ISSCC) Digest of Technical Papers, San Francisco, California, Feb. 22-26, 2015, pp. 228-229.

Lin et al., "An Inductive Power and Data Telemetry Subsystem With Fast Transient Low Dropout Regulator for Biomedical Implants", IEEE Transactions on Biomedical Circuits and Systems, vol. 10, Issue 2, Apr. 2016, pp. 435-444.

Lo et al., "A 176-Channel 0.5cm3 0.7g Wireless Implant for Motor Function Recovery after Spinal Cord Injury", IEEE International Solid-State Circuits Conference (ISSCC), San Francisco, California, Jan. 31-Feb. 4, 2016, 3 pgs.

Lombardo et al., "16.7 A fully-integrated half-duplex data/power transfer system with up to 40Mb/s data rate, 23mW output power and on-chip 5kV galvanic isolation", 2016 IEEE International Solid-State Circuits Conference (ISSCC), Jan. 31-Feb. 4, 2016, San Francisco, CA, USA, pp. 300-301, DOI: 10.1109/ISSCC.2016.7418026.

Mandal et al., "Power-Efficient Impedance-Modulation Wireless Data Links for Biomedical Implants", IEEE Transactions on Biomedical Circuits and Systems, vol. 2, Issue 4, Dec. 2008, pp. 301-315.

Middlebrook, "The General Feedback Theorem: A Final Solution for Feedback Systems", IEEE Microwave Magazine, vol. 7, No. 2, Apr. 2006, pp. 50-63.

Mirbozorgi et al., "A Single-Chip Full-Duplex High Speed Transceiver for Multi-Site Stimulating and Recording Neural Implants", IEEE Transactions on Biomedical Circuits and Systems, vol. 10, No. 3, Jun. 2016, pp. 643-653, DOI: 10.1109/TBCAS.2015.2466592.

(56) References Cited

OTHER PUBLICATIONS

Mirzaei et al., "The Quadrature LC Oscillator: A Complete Portrait Based on Injection Locking", JSSC, 2007, vol. 42, No. 9, pp. 1916-1932.
Miura et al., "A 1Tb/s 3W inductive-coupling transceiver for inter-chip clock and data link", 2006 IEEE International Solid State Circuits Conference—Digest of Technical Papers, Feb. 6-9, 2006, San Francisco, CA, USA, pp. 1676-1685.
Miura et al., "Analysis and Design of Inductive Coupling and Transceiver Circuit for Inductive Inter-Chip Wireless Superconnect", IEEE Journal of Solid-State Circuits, vol. 40, Issue 4, Apr. 2005, pp. 829-837.
Muller et al., "A Minimally Invasive 64-Channel Wireless μECoG Implant", IEEE Journal of Solid-State Circuits, Jan. 2015, vol. 50, No. 1, pp. 344-359.
Okun, "Deep-Brain Stimulation for Parkinson's Disease", The New England Journal of Medicine, Oct. 18, 2012, vol. 367, pp. 1529-1538, DOI: 10.1056/NEJMct1208070.
Okun, "Deep-brain stimulation—entering the era of human neural-network modulation", The New England Journal of Medicine, Oct. 9, 2014, vol. 371, pp. 1369-1373, DOI: 10.1056/NEJMp1408779.
Pan, "A General Theory of Wireless Power Transfer via Inductive Links", UCLA Electronic Theses and Dissertations, 2015, 45 pgs.
Pan et al., "22.7 An inductively-coupled wireless power-transfer system that is immune to distance and load variations", 2017 IEEE International Solid-State Circuits Conference (ISSCC), Feb. 5-9, 2017, pp. 382-383.
Shoaib et al., "A 0.6-107 μW Energy-Scalable Processor for Directly Analyzing Compressively-Sensed EEG", IEEE Transactions on Circuits and Systems I: Regular Papers, Apr. 2014, vol. 61, No. 4, pp. 1105-1118, DOI: 10.1109/TCSI.2013.2285912.
Shoaib et al., "Enabling advanced inference on sensor nodes through direct use of compressively-sensed signals", 2012 Design, Automation & Test in Europe Conference & Exhibition (DATE), Mar. 12-16, 2012, Dresden, Germany, pp. 437-442, DOI: 10.1109/DATE.2012.6176511.
Tan et al., "A 2.4 GHz ULP Reconfigurable Asymmetric Transceiver for Single-Chip Wireless Neural Recording IC", IEEE Transactions on Biomedical Circuits and Systems, Aug. 2014, vol. 8, No. 4, pp. 497-509, DOI: 10.1109/TBCAS.2013.2290533.
Weaver et al., "Handbook of biological effects of electromagnetic fields", Taylor & Francis Group, LLC, 2007, Third Edition, 465 pgs.
Who, "What are neurological disorders?", May 2016, retrieved from https://web.archive.org/web/20170418102437/http://www.who.int/features/qa/55/en/ on Jul. 16, 2020, 1 pg.
Xu et al., "Design Methodology for Phase-Locked Loops Using Binary (Bang-Bang) Phase Detectors", IEEE Transactions on Circuits and Systems I: Regular Papers, Jul. 2017, vol. 64, No. 7, pp. 1637-1650, DOI: 10.1109/TCSI.2017.2679683.
Yilmaz et al., "Wireless Energy and Data Transfer for In-Vivo Epileptic Focus Localization", IEEE Sensors Journal, vol. 13, No. 11, Nov. 2013.
Yousefi et al., "A Distance-Immune Low-Power 4-Mbps Inductively-Coupled Bidirectional Data Link", Symposium on VLSI Circuits, Kyoto, Japan, Jun. 5-8, 2017, pp. C60-C61.
Zierhofer et al., "High-Efficiency Coupling-Insensitive Transcutaneous Power and Data Transmission Via an Inductive Link", IEEE Transactions on Biomedical Engineering, vol. 37, No. 7, Jul. 1990, pp. 716-722.

* cited by examiner

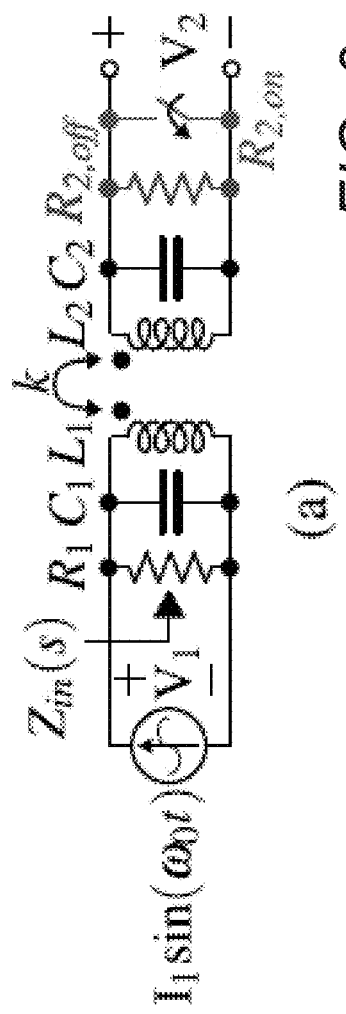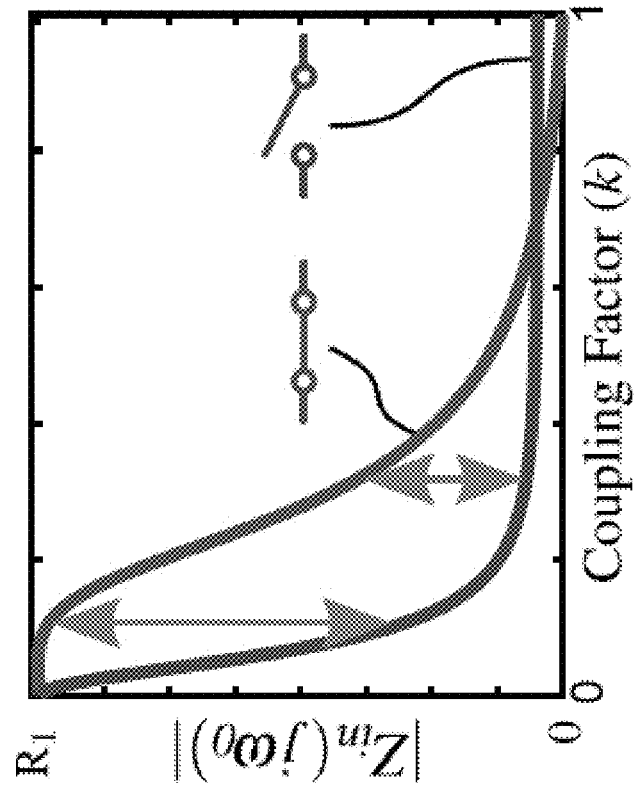
FIG. 9a
FIG. 9b

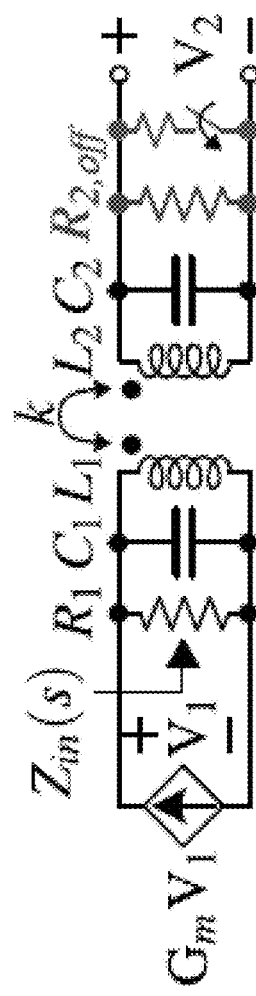
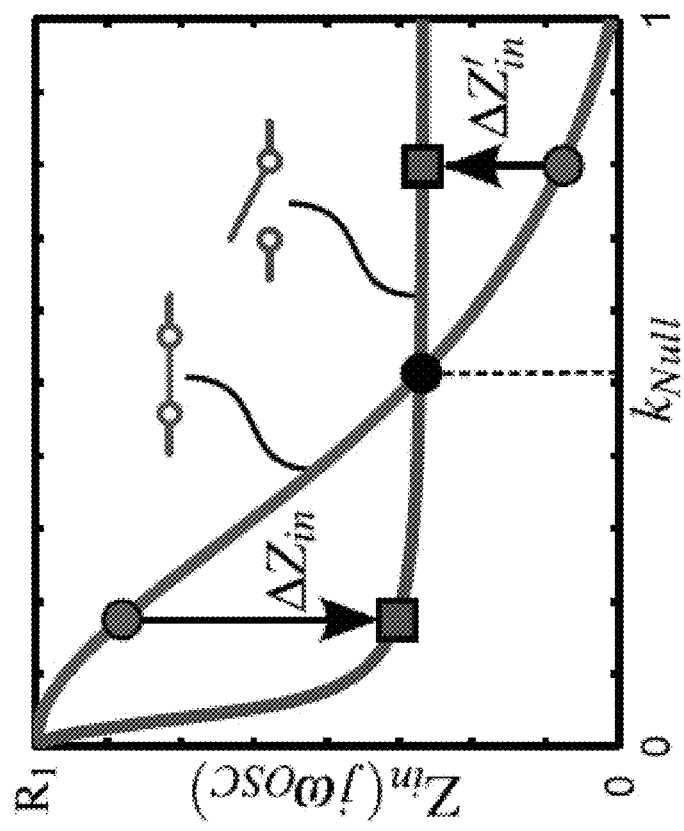
FIG. 10A
FIG. 10B

TABLE I. Comparison with the state of the art

| Reference | Size of Coils [cm] | Max. range ($R_{max}$) [cm] | Norm. max. range§ | Carrier Freq. [MHz] | Data Rate (Up/Dn) [Mbps] | Bit error rate+ | Impl. Tx/Rx power [pJ/bit] | Ext. Tx/Rx power [pJ/bit] |
|---|---|---|---|---|---|---|---|---|
| [3] | 2/1.2 | 0.5 | 0.32 | 5/10 | -/2.5 | $10^{-5}$ | - | - | - |
| [4] | 3.5/3.5 | 2 | 0.5 | 25 | 2.8/0.3 | $10^{-6}$ | 152 | - | 892 |
| [5] | 1/3 | 1 | 0.51 | 66.6 | -/20 | $8.7\times10^{-8}$ | 36 | 467 | 5000 | - |
| [6] | 3/1 | 1 | 0.51 | 50 | -/13.56 | $4.3\times10^{-7}$ | - | 12 | 180 | - |
| [7] | 3/2 | 0.5 | 0.2 | 10 | 2/- | $4.8\times10^{-4}$ | - | 162 | 960 | - |
| [8] | 6.5/4.2 | 3.5 | 0.7 | 13.56 | 6.78/0 | $10^{-7}$ | 9.5 | - | - | - |
| This Work§ | 3/3 | 4 | 1.33 | 35 | 4/2 | $5\times10^{-8}$ | 0.1 | 5 | 200 | 150 |

FIG. 21

SYSTEMS AND METHODS FOR LOW-POWER NEAR-FIELD-COMMUNICATION

CROSS REFERENCE TO RELATED APPLICATIONS

This application is a national stage of PCT Patent Application No. PCT/US2018/031902, entitled "Systems and Methods for Low-Power Near-Field-Communication" to Yousefi et al., filed May 9, 2018, which claims priority to U.S. Provisional Application No. 62/666,460, entitled "Systems and Methods for Distance-Immune Low-Power Inductively-Coupled Bidirectional Data Links" to Yousefi et al., filed May 3, 2018, and U.S. Provisional Application No. 62/503,846, entitled "Systems and Methods for Distance-Immune Low-Power Inductively-Coupled Bidirectional Data Links" to Markovic et al., filed May 9, 2017, the disclosures of which are incorporated by reference herein in their entirety.

STATEMENT REGARDING FEDERALLY SPONSORED RESEARCH OR DEVELOPMENT

This invention was made with government support under Grant Number W911NF-14-2-0043, awarded by the U.S. Army, Army Research Office. The government has certain rights in the invention.

FIELD OF THE INVENTION

The present invention generally relates to data links and, more specifically, distance-immune inductively-coupled wireless data links.

BACKGROUND

According to the World Health Organization (WHO), hundreds of millions of people, nearly one in seven of the world's population, are suffering from neurological and psychiatric disorders such as Alzheimers and Parkinsons diseases, depression, and strokes. These disorders can have serious effects on patients' daily lives and can bring a multitude of motor and non-motor manifestations. As such, there has been a growing trend to develop tools to study, diagnose, and treat these categories of diseases. In these tools, wireless data links are an integral block of the system which decreases the risk of infection in the patient, increases patient mobility, and improves their comfort and, as a result, the quality of life. Moreover, in modern closed-loop neuromodulation systems, the algorithms used can contain significant computational load, which may not be completely realizable for execution within the implanted devices within the body due to constraints on power and area. To mitigate these issues, algorithms can be implemented external to the body so as to have greater computational freedom.

Implanted devices are electronic biomedical devices used for patient monitoring, diagnostics, and various other purposes. These devices can be implanted inside a patient's body, typically by means of a surgical operation. Implanted devices can act as either sensors or stimulators. Sensors measure biosignals, such as body temperature and blood pressure, from inside the body and transmit this information to an external device. Stimulators receive information externally, such as from an external unit operated by doctors, and can produce signals within the body, such as stimulating specific nerves. Common applications of stimulators include the use of microelectrodes for diagnosing and determining treatment of brain disorders and neurological conditions.

Early implanted devices were interfaced with wires through the skin in order to receive energy and transmit data. However, this arrangement can restrict the patient's movements and require bulky, rack-mounted electronics. Furthermore, because of penetration through the skin, there is a greater risk of infection. Recent technological achievements in microtechnologies and microsystems have led to the use of inductive powering to transfer power to the implanted device. The same inductive link used to power the implant can also be used to transmit data between the implant and an external device.

SUMMARY OF THE INVENTION

Systems and methods for distance-immune inductively-coupled data links are disclosed. In one embodiment, an inductively-coupled data link system includes: an external transceiver including: an oscillator configured to generate an oscillator output; a first inductor; a first transmitter circuit for transmitting downlink data signals via the first inductor by amplitude modulating the oscillator output; a first receiving circuit for receiving uplink data signals via the first inductor; and an implanted transceiver including: a second inductor; a second receiving circuit for receiving amplitude modulated downlink data signals via the second inductor; a second transmitter circuit for modulating uplink data signals on an oscillator signal received by the second inductor; where: the external transceiver and the implanted transceiver are positioned such that an electromagnetic field produced by at least one of the first inductor and the second inductor is inductively coupled to the other inductor; and the external transceiver further includes control circuitry that controls the oscillator signal generated by the oscillator as a function of the inductive coupling of the first inductor and the second inductor.

In a further embodiment, the implanted transceiver is configured to modulate the uplink data signals on the oscillator signal received by the second inductor by amplitude modulating the oscillator signal with a data-driven switch that shorts a load on the implanted transceiver.

In another embodiment, the implanted transceiver comprises a load resistance, and the load resistance and switch on-resistance of the implanted transceiver prevent inversion of the modulated uplink signal at the external transceiver.

In a still further embodiment, the load resistance of the implanted transceiver comprises a bank of switched resistors controlled by control circuitry to limit switch on-resistance and prevent inversion of the modulation uplink signal over larger separations of the first and second inductors.

In still another embodiment, the control circuitry of the external transceiver controls the oscillator signal to control the magnitude of the amplitude modulated uplink signal as a function of the inductive coupling of the first inductor and the second inductor.

In a yet further embodiment, the inductively coupled first inductor is connected directly to the oscillator terminals such that the separation between the first and second inductors tunes the oscillation frequency.

In yet still a further embodiment, the external transceiver and the implanted transceiver each includes an analog front-end (AFE) for demodulating a received signal and a clock and data recovery (CDR) loop for providing synchronous data decisions.

In another further embodiment, the AFE includes two degenerated common-source MOSFETS with connected drains, wherein the AFE is driven at the device gates by an input differential voltage.

In still another further embodiment, the CDR includes a bang-bang phase detector as a one bit time-to-digital converter (TDC), a frequency detector for increasing acquisition range, an integral and proportional loop filter, and a digital controlled oscillator (DCO).

In a further embodiment still, the implanted transceiver includes control circuitry including a resistor bank, where the control circuitry controls the resistance of the resistor bank based upon the inductive coupling of the first inductor and the second inductor.

In another additional further embodiment, the external transceiver includes a resistor bank that adjusts channel bandwidth.

In yet another further embodiment, the level of the oscillator signal is controlled using an amplitude control loop circuit that compares the detected envelope with a DC reference.

In a further embodiment still, the oscillator has a CMOS core and is biased with a binary weighted tail current that is controlled by binary data and an input from the amplitude control loop circuit.

In a further embodiment again, the amplitude control loop circuit includes an envelope detector for measuring the amplitude of the oscillator, a high gain amplifier for comparing the detected amplitude with a reference voltage, $V_{ref}$, and a digital counter that outputs a binary word controlling the binary-weighted tail current.

In yet a further embodiment again, the amplitude control loop circuit is only active and adjusts a current source at communication start-up, and during normal operation, the amplitude control loop circuit stops and only the binary data modulates the amplitude of the oscillator.

In yet a further embodiment still, the external transceiver is configured so that at least a minimal bias current flows continuously through the oscillator during downlink communication.

In a yet further additional embodiment, the external transceiver is configured so that during uplink communication, the current source of the oscillator is kept constant at a maximum while the second transmitter circuit switches its load and thereby modulates the oscillation amplitude.

In another embodiment, an implanted transceiver, includes: an inductor; a receiving circuit for receiving amplitude modulated downlink data signals via the inductor; a transmitter circuit for modulating uplink data signals on an oscillator signal received by the inductor; and control circuitry including a resistor bank, where the control circuitry controls the resistance of the resistor bank based upon inductive coupling of the inductor.

In a further embodiment, the implanted transceiver further includes an analog front-end (AFE) for demodulating a received signal and a clock and data recovery (CDR) loop for providing synchronous data decisions.

In still a further embodiment, the AFE includes two degenerated common-source MOSFETS with connected drains, wherein the AFE is driven at the device gates by an input differential voltage.

In still a further embodiment again, the CDR includes a bang-bang phase detector as a one bit time-to-digital converter (TDC), a frequency detector for increasing acquisition range, an integral and proportional loop filter, and a digital controlled oscillator (DCO).

BRIEF DESCRIPTION OF THE DRAWINGS

The description and claims will be more fully understood with reference to the following figures, data graphs, and diagrams, which are presented as exemplary embodiments of the invention and should not be construed as a complete recitation of the scope of the invention.

FIG. 9a illustrates modulation at a fixed frequency (e.g. $w_0$) in accordance with an embodiment of the invention.

FIG. 9b illustrates a graph of modulation index shrinking as coil separation changes in accordance with an embodiment of the invention.

FIG. 10a illustrates a finite switch on resistance in accordance with an embodiment of the invention.

FIG. 10b illustrates a graph of a null point with respect to a coupling factor, K.

FIG. 21 illustrates a table of measured performance in accordance with an embodiment of the invention.

Figure 1:
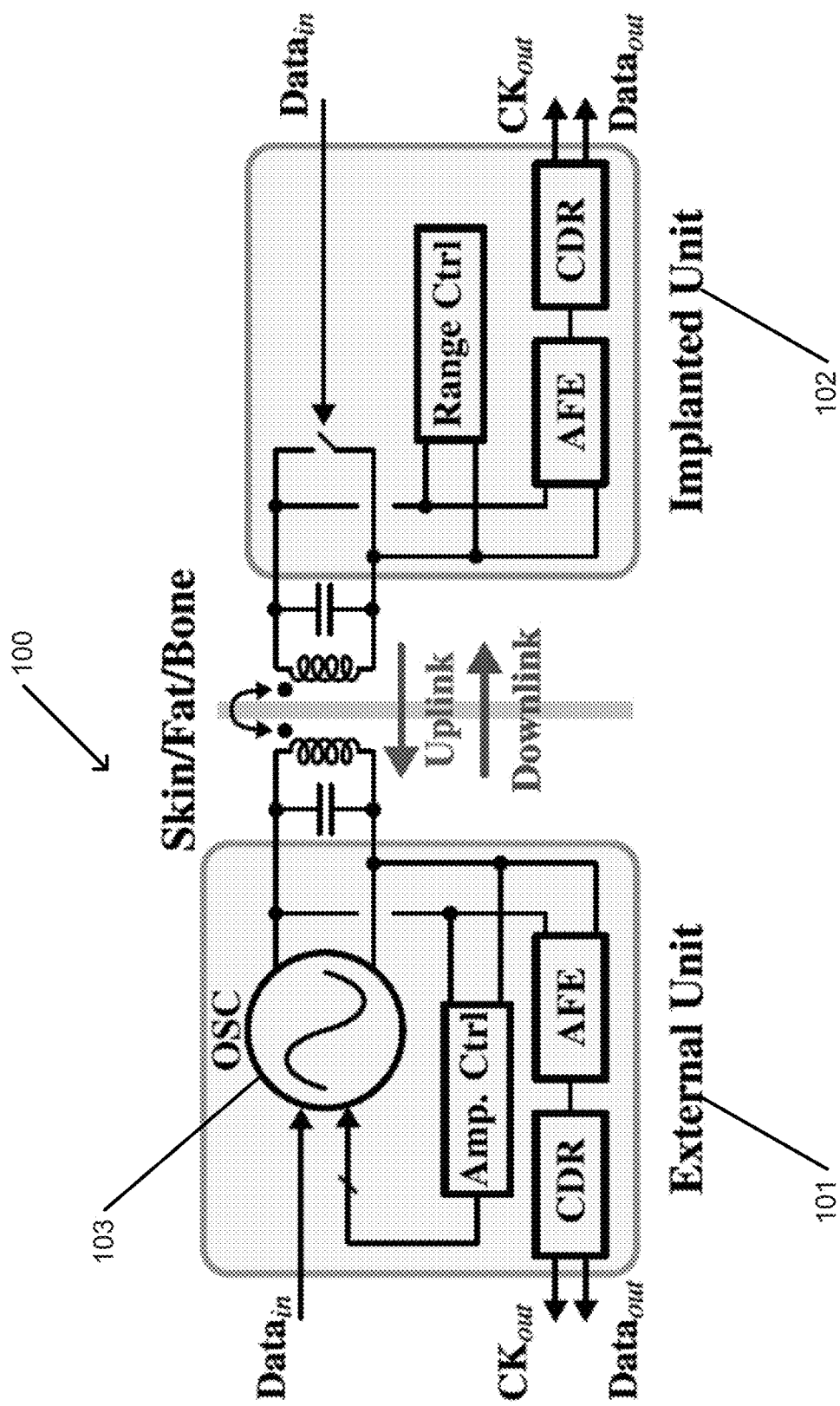
FIG. 1 illustrates a data link system in accordance with an embodiment of the invention.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

DETAILED DESCRIPTION

Turning now to the drawings, systems and methods for distance-immune inductively-coupled data links are illustrated. Such data telemetry links can be used in many different applications, such as but not limited to biomedical implants for relaying monitoring data to an external unit outside the human body. In many embodiments, the data link system is a bidirectional half-duplex wireless system using near-field inductive coupling between an implanted system and an external transceiver. In some embodiments, the data link system is based on a free-running oscillator tuned by coupled resonators. The use of an oscillator-based power link can allow for stable power over different inductor distances, or coil distances. In some embodiments, the data link system includes receivers on both sides of the link, where each receiver is composed of a detector, such as but not limited to an analog front-end ("AFE"), and a clock and data recovery ("CDR") loop. The AFE can be used for envelope detection, amplification, filtering, and bit slicing. The CDR can be used for reconstructing the clock and data signals from received signals. In a number of embodiments, the external transceiver includes an amplitude control loop circuit to control the level of the oscillator to a desired value. In several embodiments, the implanted system includes a range control circuit used to optimize operation due to variance in distances between the external device and the implanted device. In further embodiments, the range control circuit is implemented using a resistor bank.

As described above, it is important to have an implantable low-power wireless data link to communicate with a powerful external unit, which has access to more computational resources. In addition to ultra-low power consumption, the data link may need to have enough bandwidth to transfer the recorded data at the neural sensing front-ends to the outside (uplink), and the configuration data from external module to the inside (downlink). For instance, to have 500 sensing sites which are recording neural activity at a sampling rate of 0.5 kilo samples per second (kS/s) with a resolution of 16 bits (e.g. for local field potential (LFP) recording), the data link may need to support a data rate of 4 megabits per second (Mbps). Another important goal for a robust data link is insensitivity of the link performance to distance variation. Due to patient movements and different surgical placement for different patients, the distance between internal and external transceivers is very likely to vary; and therefore, many embodiments of the system provide a design that addresses these challenges. Also, in order to avoid excessive power loss in the tissue, the carrier frequency may be kept to a few tens of MHz where the loss is infinitesimal. Accordingly, many embodiments of the data link system provide an ultra-low power, yet robust data link, that can cover a range of 4 cm while the internal transceiver consumes only 300 nW for receiving uplink transmissions at 4 Mbps and 10 µW for transmitting downlink transmissions at 2 Mbps.

DataLink Architecture

A data link system in accordance with an embodiment of the invention is illustrated in FIG. 1. In particular, FIG. 1 illustrates a data link 100 that includes two separate modules: an external unit 101, which can sit on the skin, and an implanted unit 102, that may be embedded in the body. The link may have two coupled resonators at its core, each of which can resonate at a particular frequency. In several embodiments, each resonator may resonate at approximately 35 MHz. For simplicity, amplitude modulation can be employed in both the uplink and downlink. By using an amplitude modulation scheme, moreover, a simple non-coherent receiver may be even able to detect the data, and therefore the reception power consumption can be maintained at a low level.

As illustrated in FIG. 1, on the primary side of the link, a free running oscillator (OSC) 103 may generate the carrier. In the downlink, from the external unit to the implant, binary data may modulate the carrier amplitude between two levels. In the reverse, uplink direction, the carrier can be modulated with a data-driven switch that shorts the load on the implant. The modulated load may then be transformed across the oscillator terminals and may force oscillation at one of the two amplitudes. Since the load modulation may involve only the activation of a switch, the power consumption can be very low.

As illustrated in FIG. 1, the coupled resonators can be connected directly to the oscillator terminals whereby the resonators may tune the oscillation frequency. The link may also include non-coherent receivers on both sides. Each receiver may include an analog front-end (AFE) for demodulating the received waveform, and a clock and data recovery (CDR) loop where synchronous data decision may take place.

On the primary side (i.e., external unit), an amplitude control loop may adjust the carrier amplitude at the link power-up. The loop may become later deactivated during the normal operation of the link while the bits are sent over the air. Furthermore, a range control unit on the secondary side (i.e., implanted unit) may control the quality factor of the secondary resonator (Q2). Although FIG. 1 illustrates a particular architecture of a data link system, any of a variety of architectures may be utilized as appropriate to the requirements of specific applications in accordance with various embodiments of the invention. Operations of data link systems in accordance with a number of embodiments of the invention are described below.

Operation

Figure 2:
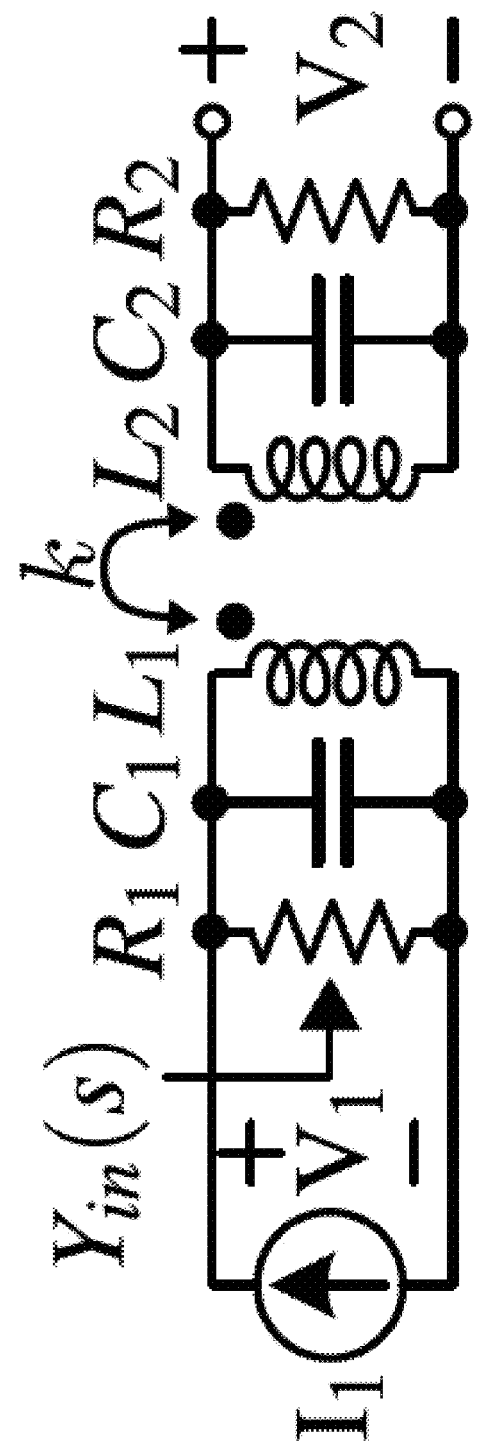
FIG. 2 illustrates circuit properties of two coupled resonators in accordance with an embodiment of the invention.
Figure 3:
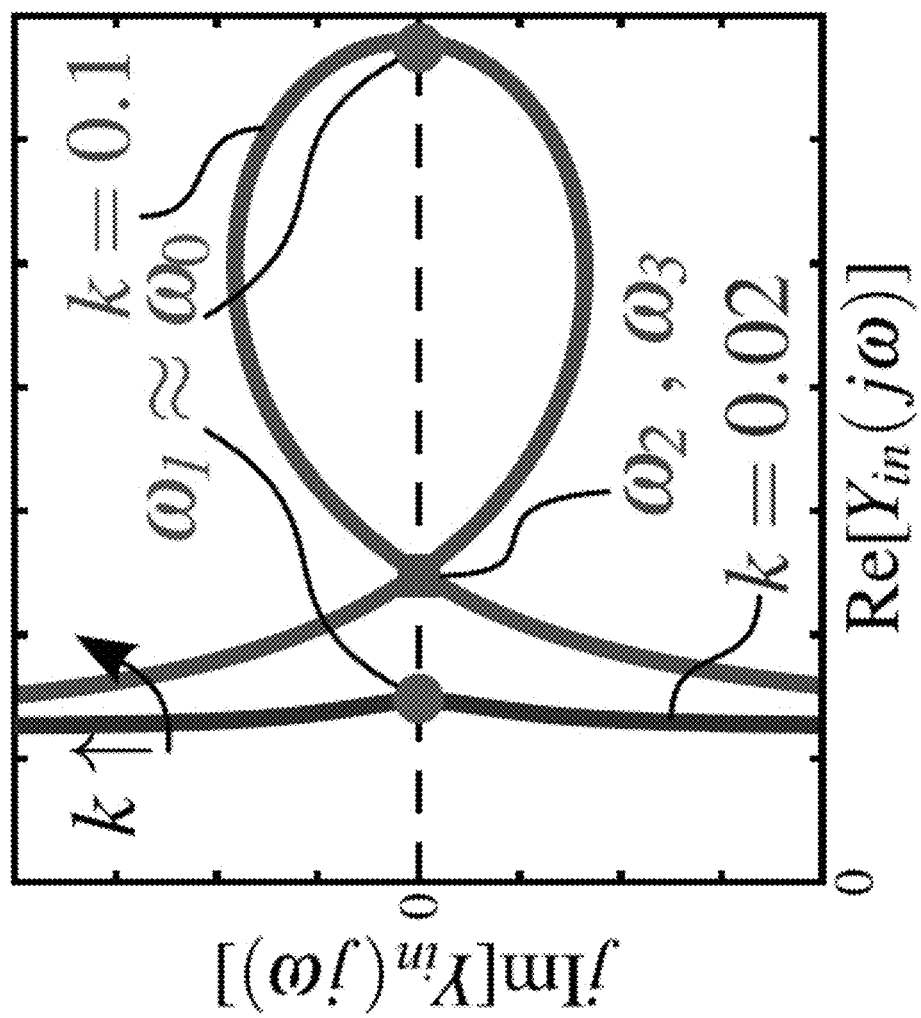
FIG. 3 illustrates a graph of an example of the input admittance plot in a complex plain, where frequency is a parameter.

As described above, in many embodiments the coupled resonators can tune the oscillator. The circuit properties of two coupled resonators in accordance with an embodiment of the invention are illustrated in FIG. 2. Note that each uncoupled resonator can have the same resonance frequency of $\omega_0 = 1/\sqrt{LC}$. Once coupled, the system of two resonators can have multiple possible resonance frequencies as a function of coupling factor (k). To better illustrate this fact, the input admittance, $Y_{in}$, across the primary terminals can be examined. FIG. 3 illustrates an example of the input admittance plot in a complex plane, where frequency is a parameter. In this plot, resonant frequencies occur where the admittance curves intersect the real axis (Re[$Y_{in}$]=0). Therefore, when the coils are far apart (e.g. k=0.02), there is just one intercept point with the real axis, in other words, one resonant frequency. However, when the coils are close together (e.g. k=0.1), three resonances can appear.

Figure 4:
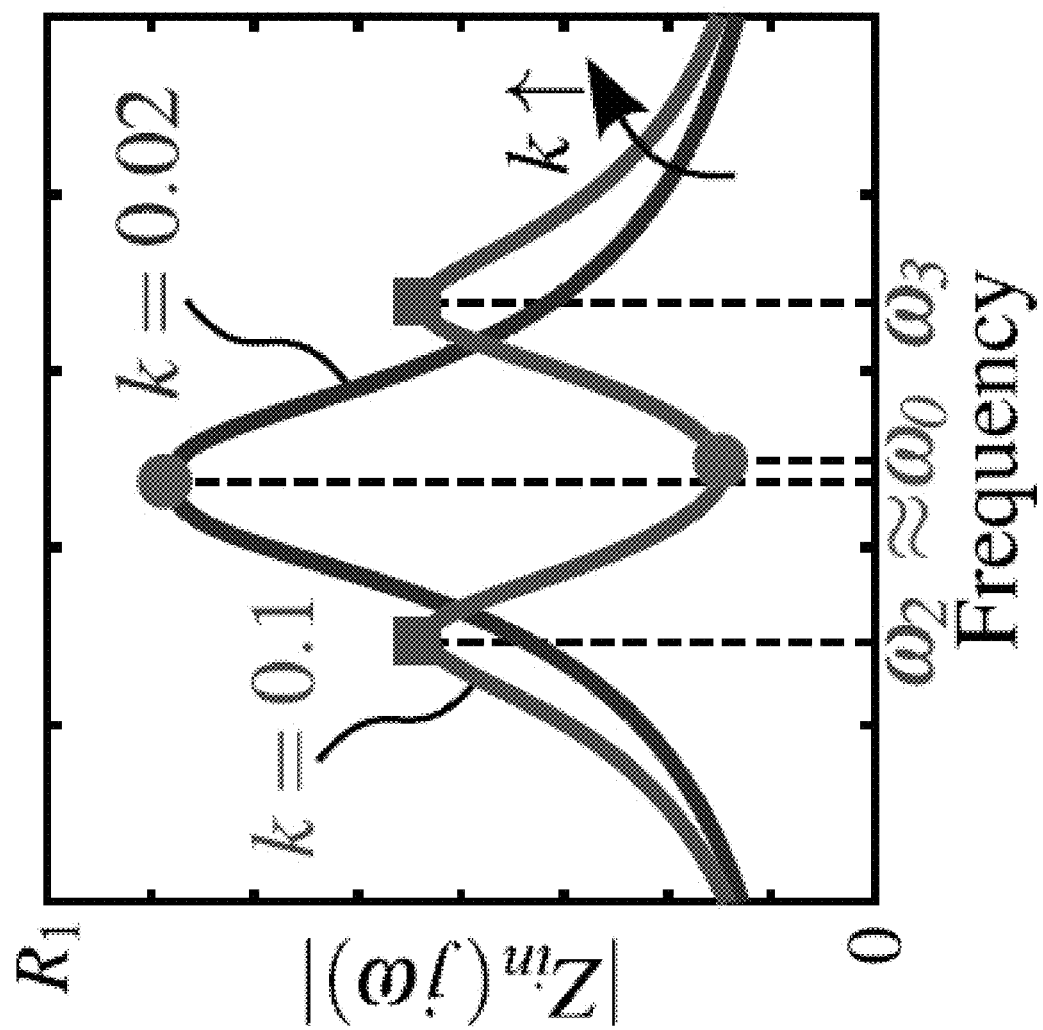
FIG. 4 illustrates a graph of an example of the impedance curves that correspond with the admittance complex plots illustrated in FIG. 3.

These resonance frequencies can be better illustrated in a graph of the input impedance magnitude plotted versus frequency. FIG. 4 illustrates an example of the impedance curves that correspond with the admittance complex plots illustrated in FIG. 3. When the coils are far apart, the impedance function may have one resonance frequency at the peak equal to $\omega_1$, given by $\omega_0\sqrt{1-k^2}$. In this expression, k appears in second-order and since k is typically much lower than 1, the resonance frequency can be also considered to be close to $\omega_0$. Once the coils come close together, bifurcation may occur in the impedance peaks; and therefore, the impedance function can have three resonance frequencies: one close to $\omega_0$ (the trough, at $\omega_1$), and two split frequencies around that (the peaks, at $\omega_2$ and $\omega_3$). The two latter resonance frequencies, in this case, are approximately equal to $\omega_0/\sqrt{1\pm k}$. Since, in the denominator, k comes in first-order, the two resonance frequencies start to bifurcate as k increases. The accurate values of the split frequencies have been derived as described in detail in U.S. Provisional Application 62/666,460 filed on May 3, 2018 entitled "Systems and Methods for Distance-Immune Low-Power Inductively-Coupled Bidirectional Data Links", the entirety of which is incorporated herein by reference.

The transition between these two cases can occur at a critical coupling factor, $k_C$, which can be roughly equal to $1/Q_2$, where $Q_2$ is the uncoupled quality factor of the secondary resonator. A more accurate expression for the critical coupling factor has also been derived as described in detail below. Although FIG. 2 illustrates a particular circuit design for coupled resonators, any of a variety of circuit designs may be utilized as appropriated to the requirements of specific applications in accordance with embodiments of the invention.

Figure 5:
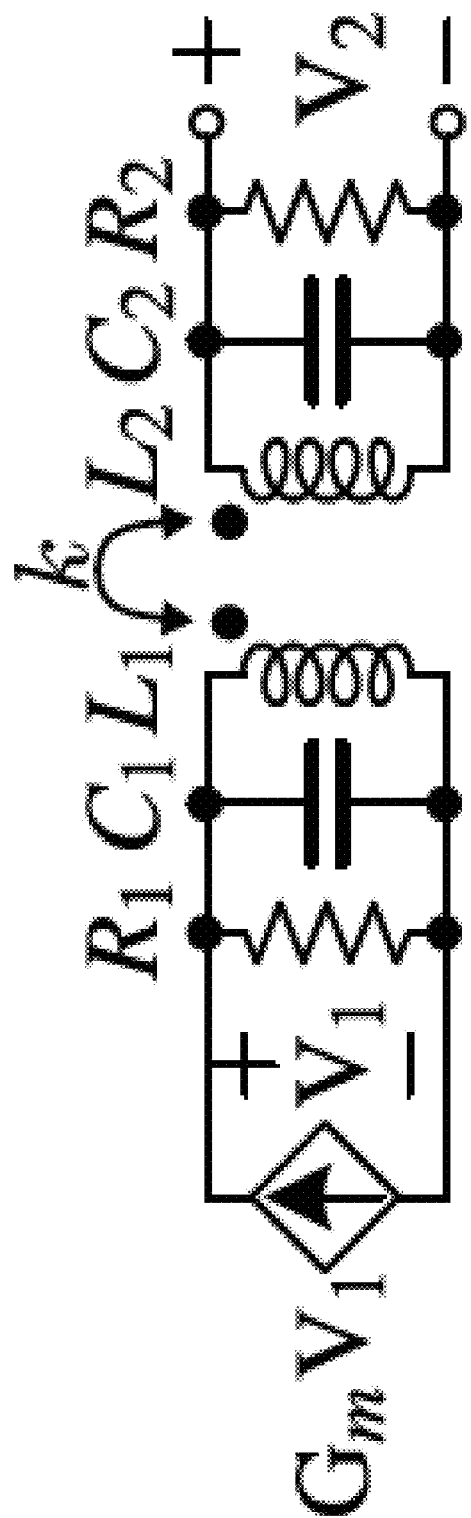
FIG. 5 illustrates an oscillator circuit design that includes coupled resonators in accordance with an embodiment of the invention.
Figure 6:
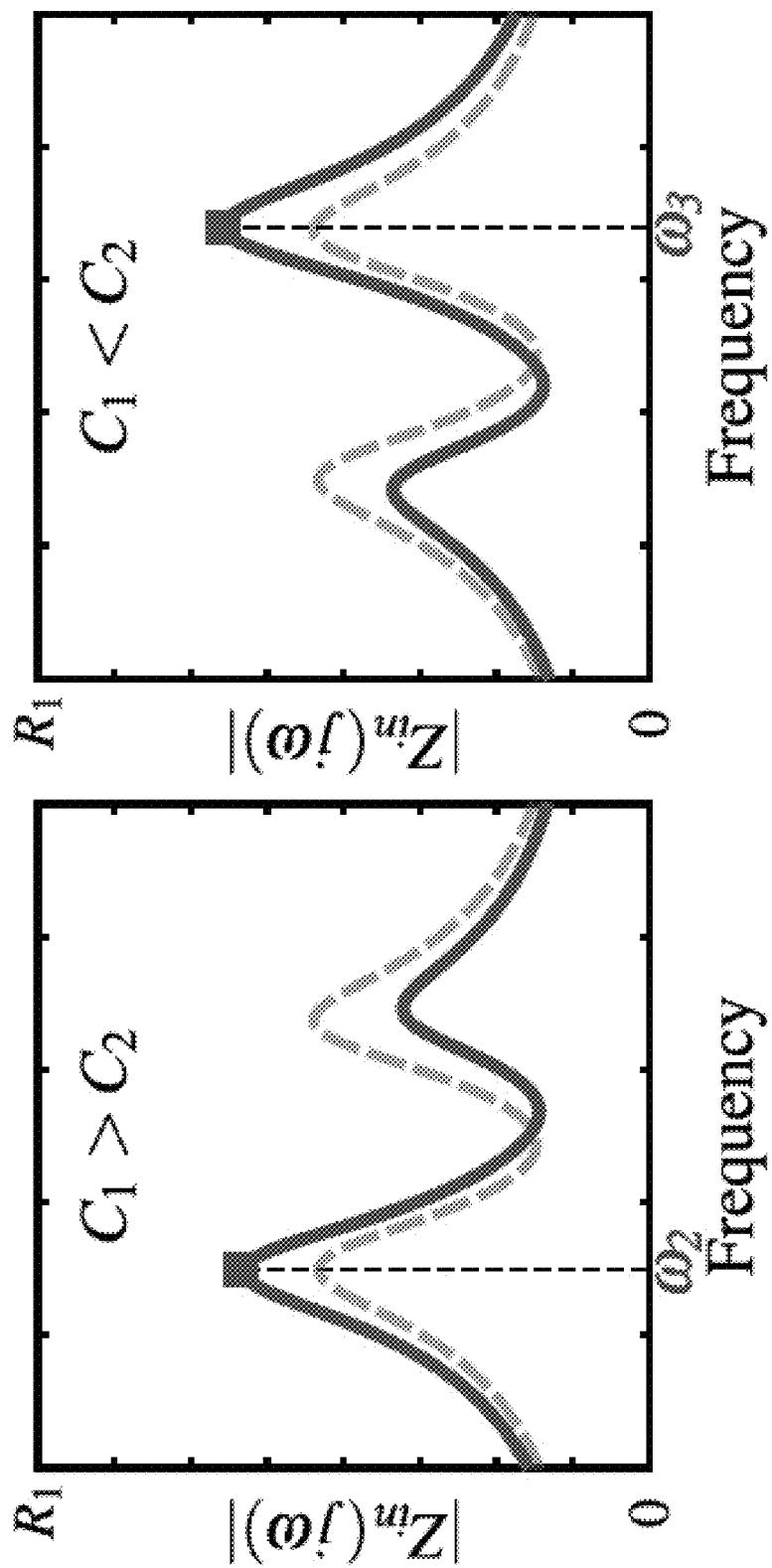
FIG. 6 illustrates graphs of stable oscillation frequencies when $k>k_c$ in accordance with an embodiment of the invention.

In many embodiments, an oscillator can be built with the coupled resonators as its tuning circuit by applying a negative conductance, $-G_m$, across its primary terminals. An oscillator circuit design that includes coupled resonators in accordance with an embodiment of the invention is illustrated in FIG. 5. Furthermore, FIG. 6 illustrates a graph showing stable oscillation frequencies when k>$k_c$. Accordingly, the circuit can oscillate at one of the peak frequencies: if <$k_c$, it can oscillate at $w_1$, and if k>$k_c$, the oscillation can appear at either $w_2$ or $w_3$. In practice, the capacitors on the two sides of the inductive link, $C_1$ and $C_2$, may be unequal and that can select the oscillation frequency. For instance, if $C_1$>$C_2$, the two peaks in impedance magnitude may be mistuned, and oscillation may take place at the frequency of the higher peak, $w_2$. This happens because, by presenting such an impedance, with two unequal peaks, to the oscillator terminals, the loop gain in the oscillator may be larger at the frequency of the higher peak. Thus, during the oscillation start-up, the envelop of oscillation at the frequency of the higher peak arises more rapidly from noise level than that of the lower peak. This faster growth may then drive the non-linear devices into saturation, which may cause the loop gains at the both frequencies to drop significantly; and thereby, the oscillation at the frequency of the higher peak dominates. In many embodiments, during an oscillator design, by deliberately choosing a slightly larger $C_1$, the oscillation frequency may be dictated to be $w_2$ when k>$k_c$. Although FIG. 5 illustrates a particular circuit architecture for an oscillator, any of a variety of architectures may be utilized as appropriate to the requirements of specific applications in accordance with embodiments of the invention.

Fundamental Limits to Range
Downlink

Figure 7A:
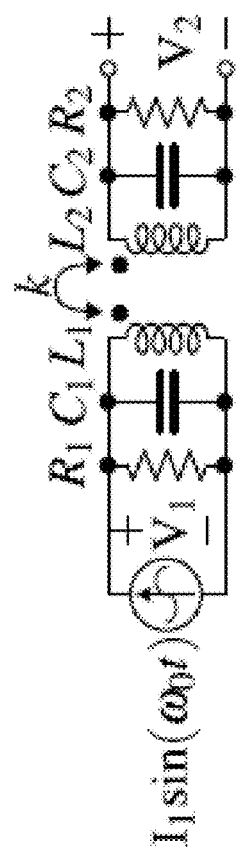
FIG. 7a illustrates modulation at a fixed frequency (e.g. $w_0$) in accordance with an embodiment of the invention.

In order to provide a downlink's immunity to distance, the transimpedance, $Z_{21}(s)=V_2/I_1$, is discussed below and illustrated in FIGS. 7a-7d, which demonstrate a downlink distance immunity in accordance with an embodiment of the invention. In particular, FIG. 7a illustrates modulation at a fixed frequency (e.g. $w_0$), FIG. 7b illustrates the manner in which transimpedance magnitude drops as the coils separation changes, FIG. 7c illustrates modulation with an oscillator (i.e., at $w_{osc}$), and FIG. 7d illustrates transimpedance magnitude remains unchanged as the coils come close together.

Figure 7B:
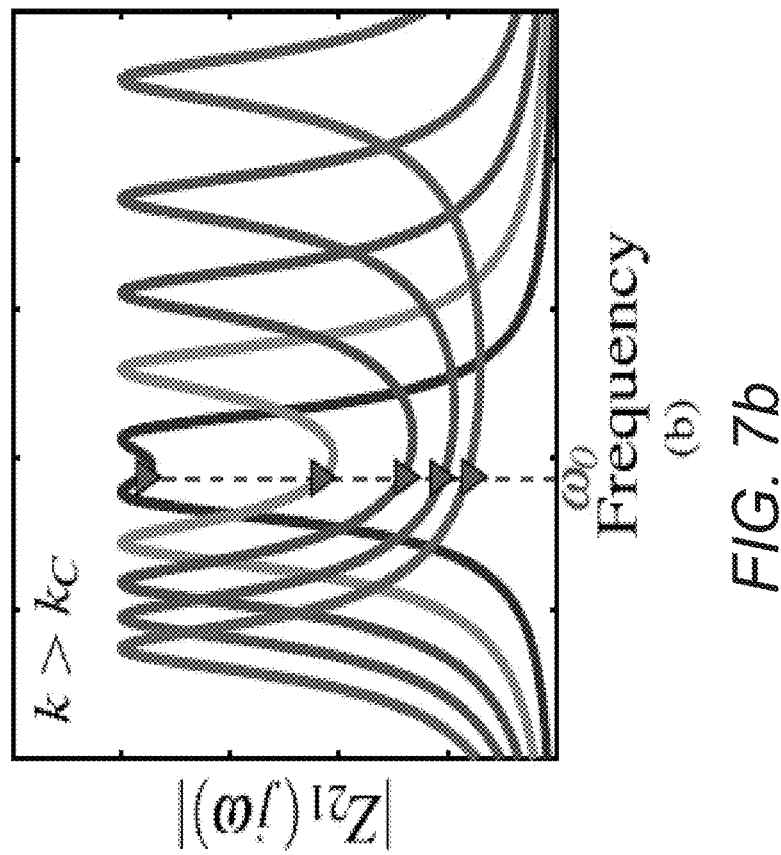
FIG. 7b illustrates a graph of transimpedance magnitude drops as coils separation changes in accordance with an embodiment of the invention
Figure 7C:
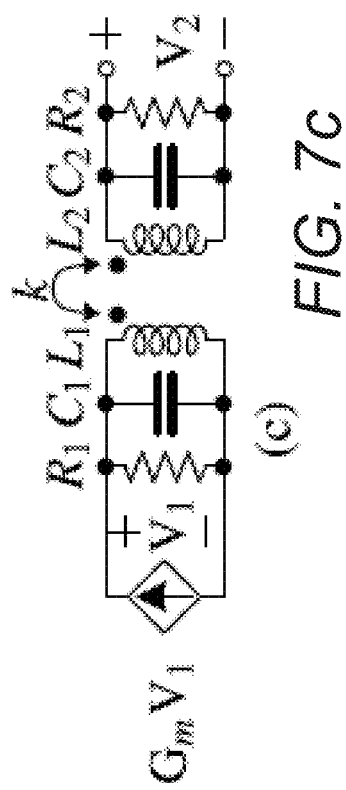
FIG. 7c illustrates modulation with an oscillator (i.e., at $w_{osc}$), in accordance with an embodiment of the invention.
Figure 7D:
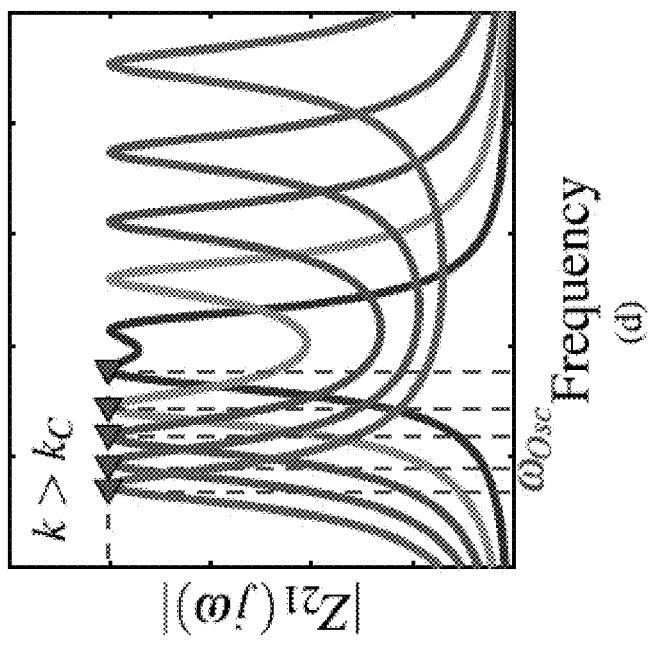
FIG. 7d illustrates a graph of transimpedance magnitude remaining unchanged as coils come close together in accordance with an embodiment of the invention.
Figure 8:
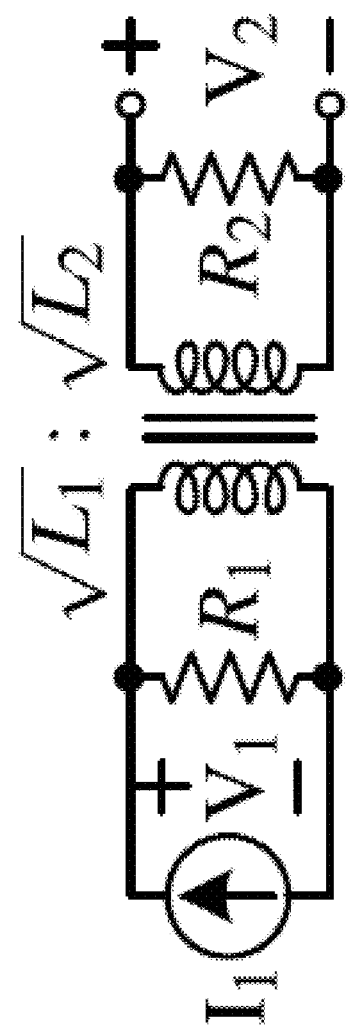
FIG. 8 illustrates a circuit modeled as an ideal transformer with a turn ratio that is independent of distance and that depends on the self-inductances of the two coils, $\sqrt{L_1}:\sqrt{L_2}$ in accordance with an embodiment of the invention.

For a link driven by an oscillator at a fixed frequency (e.g. $w_0$), as the coils come together and if the frequency remains constant, the transimpedance magnitude can drop significantly, as illustrated in FIG. 7b. In other words, the load voltage, $V_2$, can change considerably as the distance varies. However, that is not the case with a free running oscillator which can tune itself to the frequency of the peaks. An example of a free running oscillator that can tune itself to the frequency of peaks in accordance with an embodiment of the invention is illustrated in FIG. 7c. As illustrated in FIG. 7d, while the oscillation frequency is changing adaptively, unlike the case illustrated in FIG. 7a, the load voltage may remain constant as the coils come together. At the frequencies of the peaks, the circuit can be modeled as an ideal transformer whose turn ratio is independent of distance and may depend on the self-inductances of the two coils, $\sqrt{L_1}$:$\sqrt{L_2}$, as illustrated in FIG. 8 in accordance with an embodiment of the invention. Considering this model, it is evident that the load voltage may remain stable as the distance changes. This model is discussed in more detail in U.S. Provisional Application 62/666,460 filed on May 3, 2018 entitled "Systems and Methods for Distance-Immune Low-Power Inductively-Coupled Bidirectional Data Links", the entirety of which is herein incorporated by reference. Although FIGS. 7a-7c illustrate a particular circuit architecture of a free running oscillator, any of a variety of architectures may be utilized as appropriate to the requirements of specific applications in accordance with embodiments of the invention. Furthermore, although FIG. 8 illustrates a link modeled as an ideal transformer, any of a variety of circuit models may be used as appropriate to the requirements of specific applications in accordance with various embodiments of the invention.

Uplink

Figure 9C:
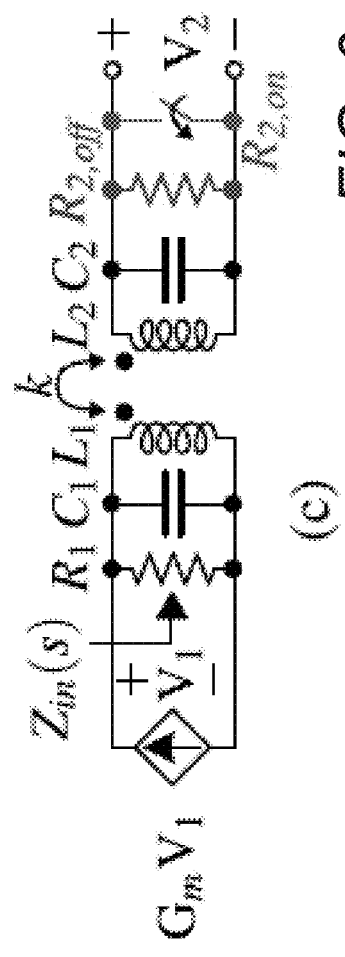
FIG. 9c illustrates modulation with an oscillator (i.e., at $w_{osc}$) in accordance with an embodiment of the invention
Figure 9D:
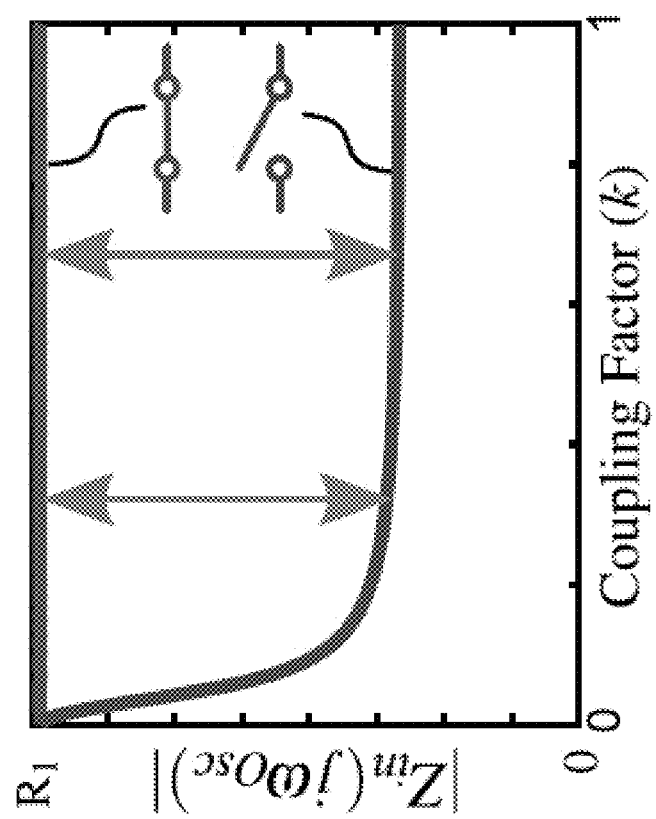
FIG. 9d illustrates a graph illustrating that a large modulation index is preserved in accordance with an embodiment of the invention.

Uplink distance immunity in accordance with an embodiment of the invention is illustrated in FIGS. 9a-9d. In particular, FIG. 9a illustrates modulation at a fixed frequency (e.g. $w_0$), FIG. 9b illustrates that the modulation index shrinks as the coil separation changes, FIG. 9c illustrates modulation with an oscillator (i.e., at $w_{osc}$), and FIG. 9d illustrates that a large modulation index is preserved.

In the uplink direction, when the switch is open, the load resistor can be $R_{2,off}$, as illustrated in FIG. 9a. However, when the switch is closed, the resistance may lower to $R_{2,on}$ which ideally is zero Ohm. This switching action (changing between $R_{2,off}$ and $R_{2,on}$) can transform into a change in the impedance appearing across the oscillator ($Z_{in}$). FIG. 9b indicates the modulation index, which can be the difference between the two input impedance curves as functions of distance (k): when the switch is open and when it is closed. Therefore, if the carrier frequency remains constant, modulation index may shrink as the distance varies. As can be seen, the modulation index may even go to zero if the two resonators are brought close together. However, in modulation with a free running oscillator, as illustrated in FIG. 9c in accordance with an embodiment of the invention, the large modulation index can be preserved, as illustrated in FIG. 9d. The modulation index is of essence in data reception because it is equivalent to eye opening at the receiver, thus the larger the modulation index, the bigger the eye, the lower the error rate. Although FIG. 9c illustrates a particular circuit architecture of a free running oscillator, any of a variety of circuit architectures may be utilized as appropriate to the requirements of specific applications in accordance with various embodiments of the invention.

In a practical case that the switch has non-zero on-resistance, the range of operation can be compromised. FIG. 10a illustrates a finite switch on-resistance in accordance with an embodiment of the invention. In several embodiments of the data link system, the switch on-resistance is approximately 10Ω~20Ω. As the load resistance, $R_2$, is switched between the two values of $R_{2,on}$ and $R_{2,off}$, the impedance appearing across the oscillator can change as a function of coupling factor, as illustrated in FIG. 10b illustrating a null point. In this case, when the coils come together even with a free running oscillator, the modulation index may pinch off. As can be seen, when coils come even closer to each other, the modulation index reverses sign. Although FIG. 10a illustrates a particular circuit architecture of a finite switch with on-resistance, any of a variety of circuit architectures may be utilized as appropriate to the requirements of specific applications in accordance with various embodiments of the invention.

Figures 11A, 11B, 11C:
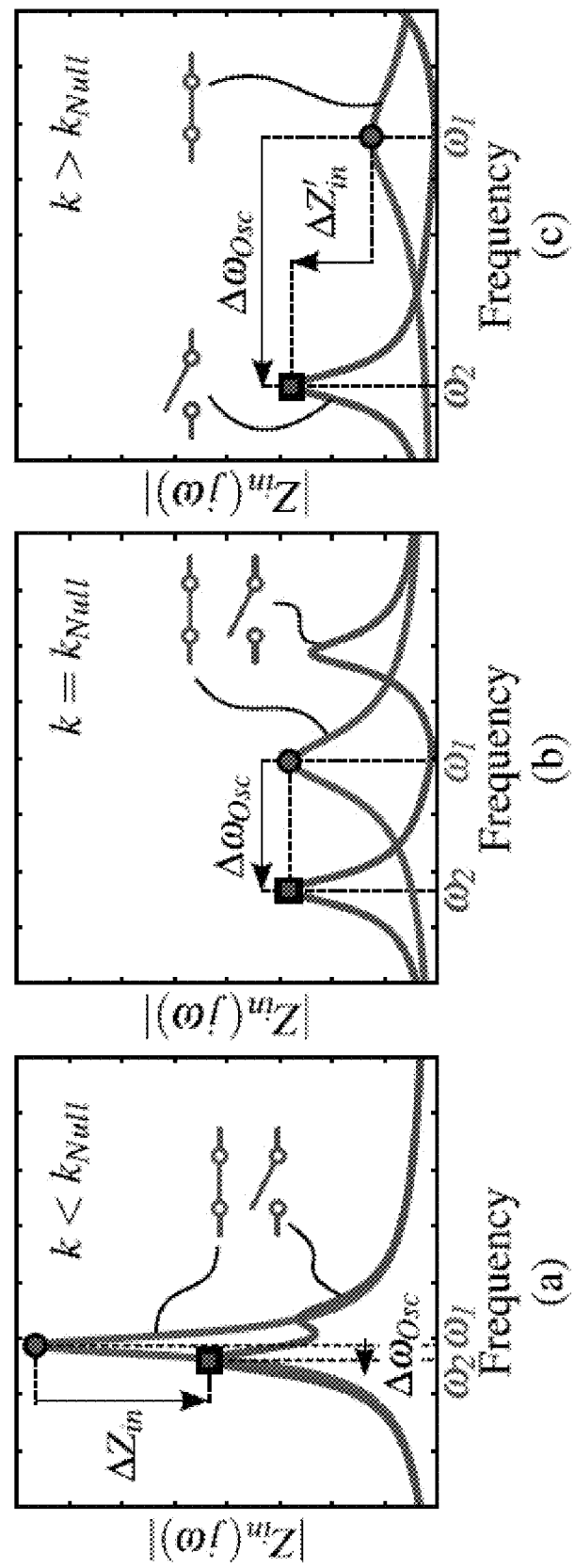
FIGS. 11A-C illustrate graphs of input impedance magnitude plots vs. frequency in accordance with an embodiment of the invention.

This sign inversion can be perceived better by looking at the input impedance as a function of frequency. In particular, FIGS. 11a-11c illustrate a graph of input impedance magnitude plots vs. frequency, with FIG. 11a illustrating when $k<k_{Null}$, FIG. 11b illustrating when $k=k_{Null}$, and FIG. 11c illustrating when $k>k_{Null}$.

In particular, FIG. 11a corresponds with the region below the null point ($k<k_{Null}$). In this region, opening the switch may lower the magnitude of the peak, and causes a minor shift to the frequency of oscillation. On the other hand, for the region above the null point ($k>k_{Null}$), as shown in FIG. 11c opening the switch may raise the magnitude of peak while significantly changing the frequency of oscillation. However, at the null point, the change in the state of the switch may only shift the frequency of oscillation whereas the impedance peak can remain unchanged, as illustrated in FIG. 11b. Since the envelope detector may be oblivious to the frequency shift, it may not detect the change in the switch state, and therefore, the link may fail.

Overall, there may be two regions of operation, and there may be a data inversion from one region to the other. In several embodiments of the data link system, the link may operate in the region below the null point. However, to provide a functional link, the link can be designed such that the null point lies outside the expected range of operation.

Figure 12B:
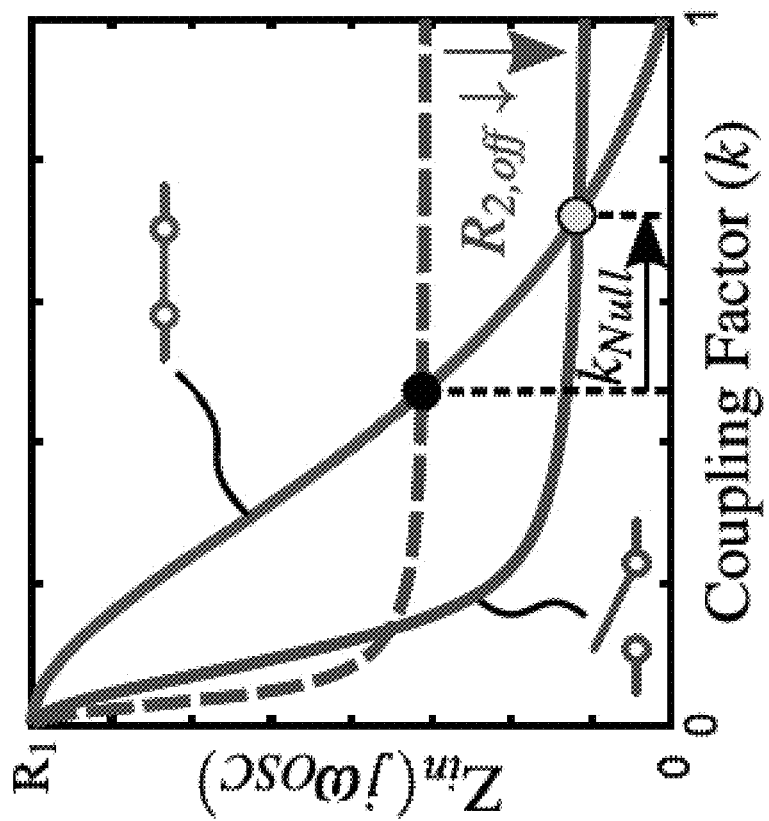
FIGS. 12A-B illustrate graphs of expanding a region of operation in accordance with an embodiment of the invention.
Figure 12A:
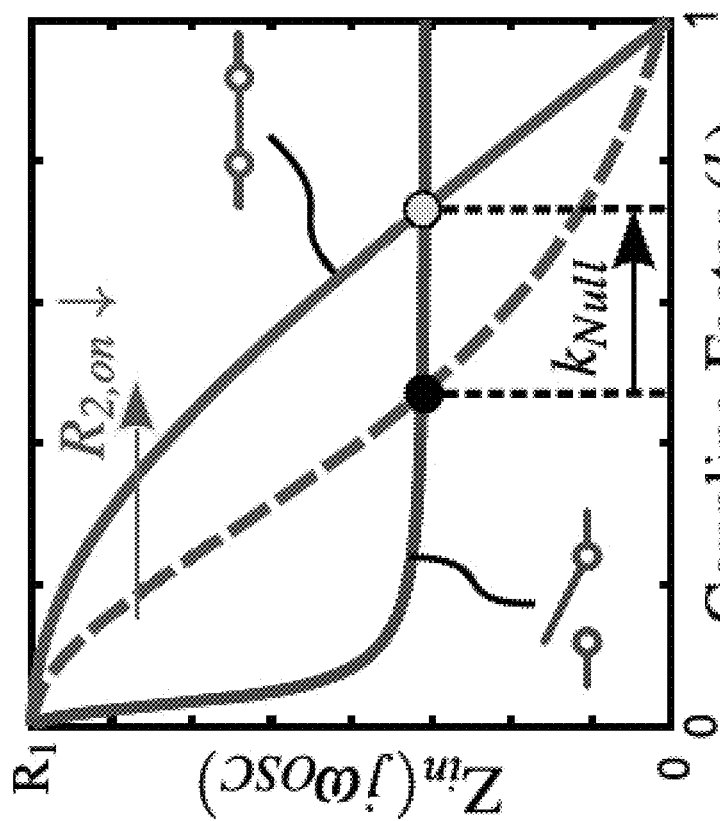

As described in more detail in U.S. Provisional Application 62/666,460 filed on May 3, 2018 entitled "Systems and Methods for Distance-Immune Low-Power Inductively-Coupled Bidirectional Data Links", the entirety of which is herein incorporated by reference, the null point can be a function of two parameters: the switch on-resistance ($R_{2,on}$) and the load resistance ($R_{2,off}$). A larger switch may have a smaller on-resistance; hence, it can be expected to approach the ideal case where the on-resistance is zero. FIG. 12 illustrates expanding a region of operation, in particular, FIG. 12a illustrates increasing the size of the switch and FIG. 12b illustrates decreasing the load resistance in accordance with an embodiment of the invention. By enlarging the size of the switch, as illustrated in FIG. 12a, the null point may shift to the right which results in a broader range of operation. In several embodiments, by pushing the null point beyond the maximum achievable coupling factor (e.g. k=0.5~0.6 in the case illustrated), the shrinking modulation index can be avoided to a great extent.

Figure 13:
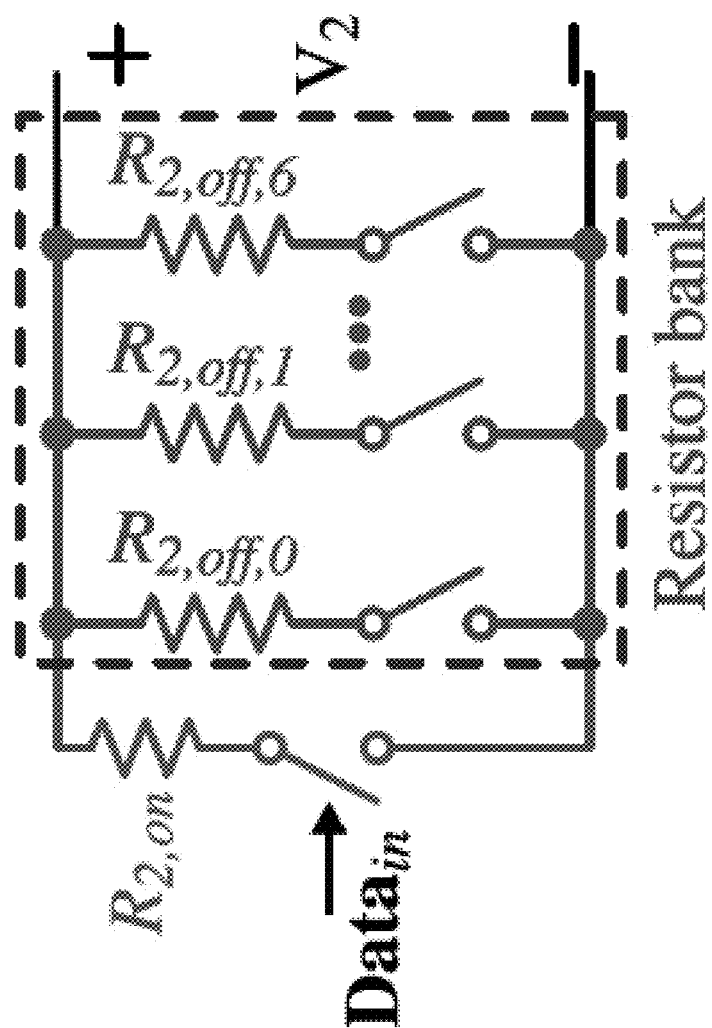
FIG. 13 illustrates a resistor bank to choose a proper $R_{2,off}$ in accordance with an embodiment of the invention.

In many embodiments, the other option of avoiding the null point is to initially choose a proper load resistance value. Several embodiments of the data link system may select the right value of load resistance according to the expected operational range and the typical switch on-resistance. However, a more convenient method may be to have tunability in the load resistance by using a resistor bank where the load resistance can be changed according to the coil separation, as illustrated in FIG. 13. In particular, FIG. 13 illustrates a resistor bank to choose a proper $R_{2,off}$. For instance, by lowering the load resistance using the resistor bank, the null point may also shift to the right, as shown in FIG. 12b. Although FIG. 13 illustrates a particular circuit for a resistor bank, any of a variety of circuit designs may be utilized as appropriate to the requirements of specific applications in accordance with various embodiments of the invention.

Circuits

Oscillator and Inductive Link

Figure 14:
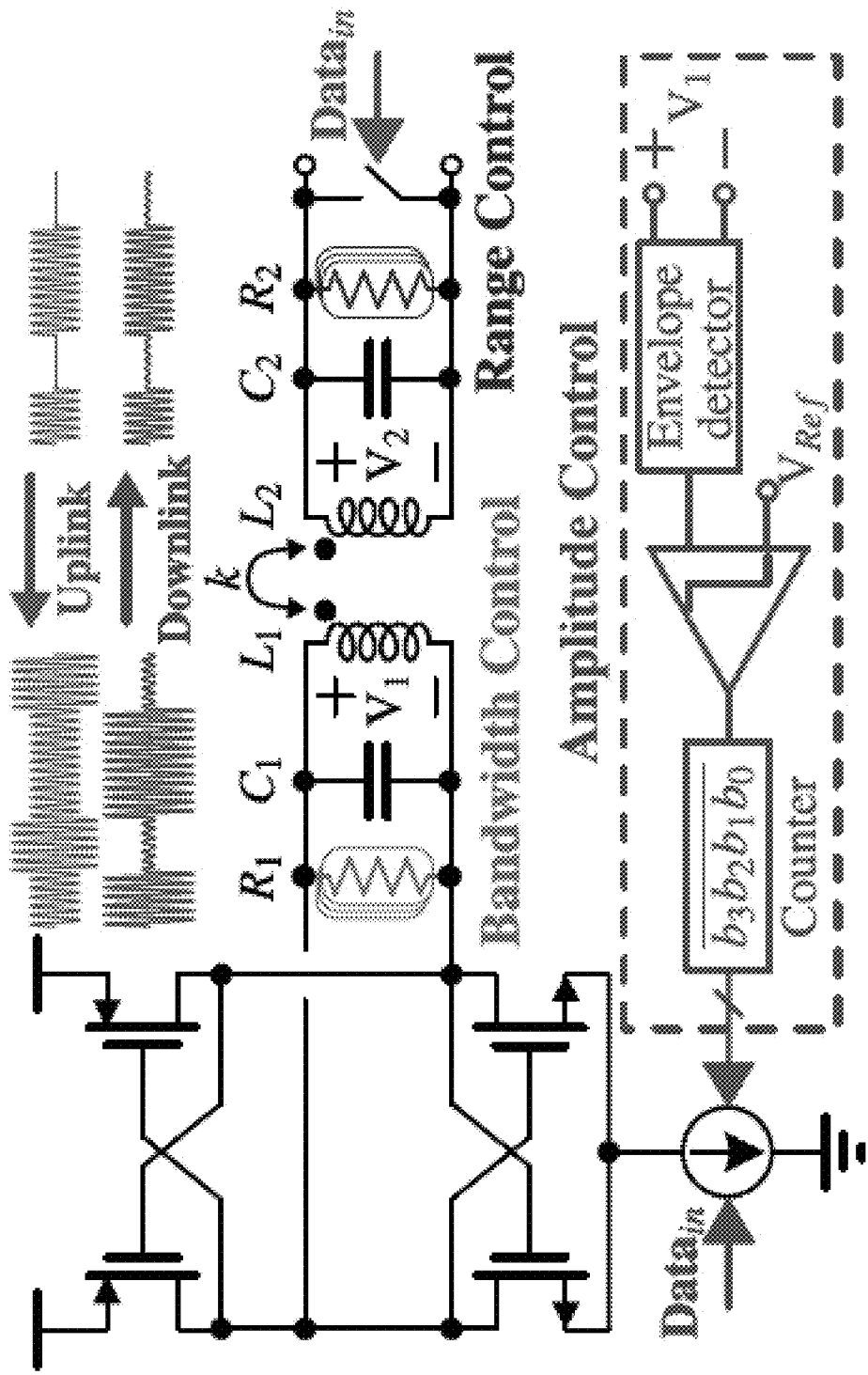
FIG. 14 illustrates a CMOS oscillator driving an inductive link in accordance with an embodiment of the invention.

As described above, in many embodiments, a link may include a resistor bank on a secondary side ($R_2$) for controlling the range of operation. A data link system that includes a resistor bank on the secondary side ($R_2$) for controlling the range of operation in accordance with an embodiment of the invention is illustrated in FIG. 14. In particular, FIG. 14 illustrates a CMOS oscillator driving the inductive link. Besides this resistor bank on the secondary side and the two coupled resonators, there may be a resistor bank on the primary side, $R_1$, which can adjust the channel bandwidth.

The oscillator may have a CMOS core which provides the maximum negative conductance for a given bias current. This may be important because the oscillator may need to function properly while it is exposed to a broad range of impedance at its terminals. The oscillator may be biased with a binary weighted tail current which can be controlled by the binary data and an input from the amplitude control loop. The amplitude control loop may only be active and adjusts the current source at the communication start-up, and during the normal operation, the loop may stop and only the binary data may modulate the amplitude of the oscillator. In downlink, to avoid high-frequency parasitic oscillation, a minimal bias current may always flow in the oscillator, causing it to have a slightly lower 100% modulation index. However, during uplink communication, the current source may be kept constant at the maximum while the switch on the secondary modulates the oscillation amplitude.

The amplitude control loop may include an envelope detector for measuring the amplitude of the oscillator, a high gain amplifier for comparing the detected amplitude with a reference voltage, $V_{Ref}$, and a digital counter which can output a binary word controlling the binary-weighted tail current. At the start-up, the input bit of the counter can be zero and the counter may begin counting and increasing the tail current linearly with time. Once the amplitude reaches the desired level, the input bit of the counter may change to one and may stop this linear search. Afterward, this word can be maintained constant while the communications is established between the two sides. This linear search may ensure that the oscillator is started-up properly and consumes an optimal amount of current for a given impedance across its terminals (for a given oscillation voltage, the lower the impedance, the higher current needed). In addition, it may be important to bias the oscillator in current-limit operation mode, and adjust the amplitude not close to the saturation. Otherwise, the oscillator may be desensitized to the variations in the impedance across its terminals and the oscillation amplitude on the primary may remain unchanged when the switch state varies on the secondary. Although FIG. 14 illustrates a particular CMOS oscillator architecture, any of a variety of oscillator architectures may be utilized as appropriate to the requirements of specific applications in accordance with embodiments of the invention.

Analog Front-End

Figure 15:
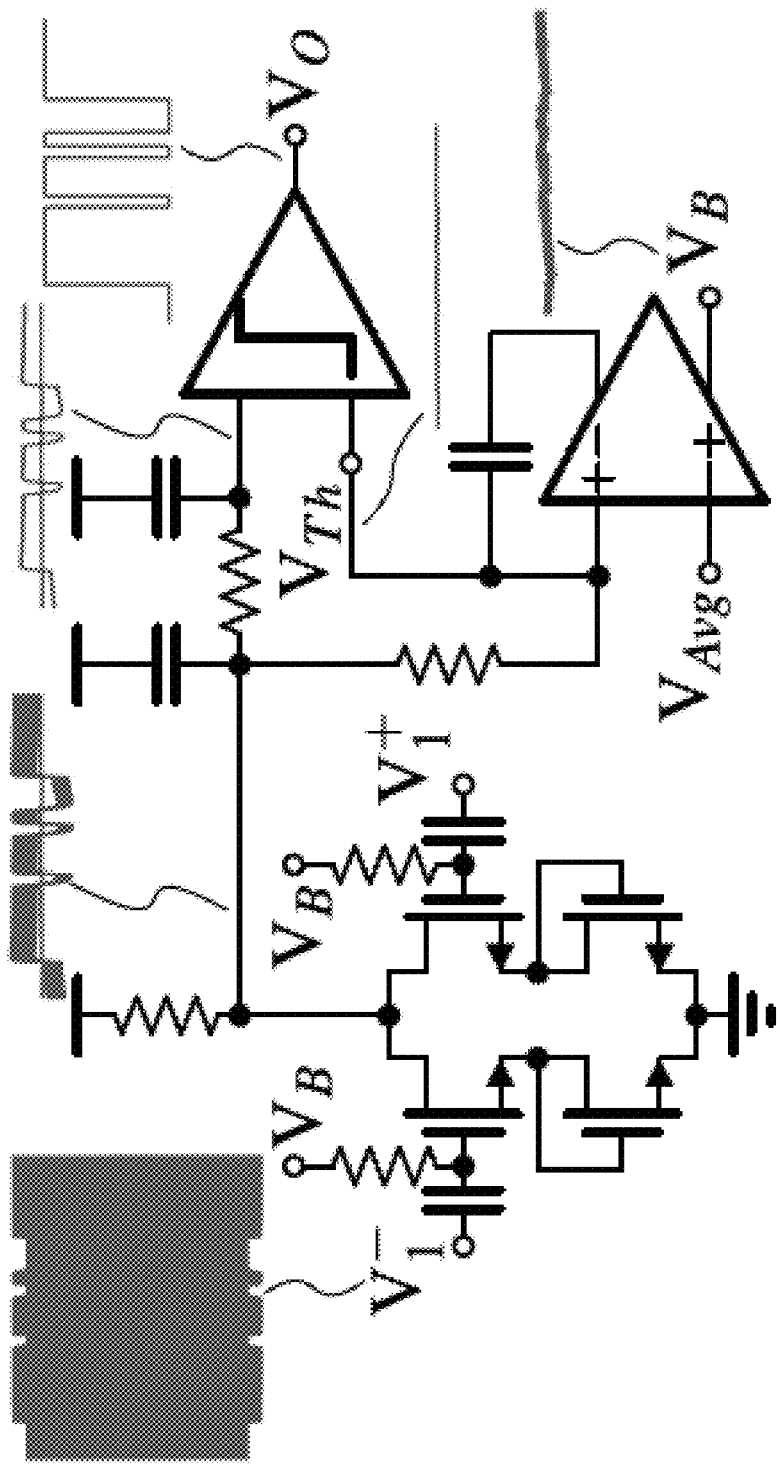
FIG. 15 illustrates an analog front-end in accordance with an embodiment of the invention.

The received waveform can be demodulated by an envelope-detector. FIG. 15 illustrates an analog front-end in accordance with an embodiment of the invention. As illustrated in FIG. 15, the detector may include two degenerated common-source MOSFETs with connected drains. The detector can be driven at the devices' gates by the input differential voltage. The stack of devices at the detector input can help the rectification voltage range extend.

This detector may have an even order voltage transfer characteristic, which may rectify the input waveform. Indeed, by going through such an even characteristic, the input waveform can be translated to DC and $2 \times f_{carrier}$, in which the signal of interest can be located around DC frequency.

For a long coils distance in uplink (e.g. 2 cm~4 cm in the illustrated embodiment), the carrier amplitude fluctuation caused by the data can be relatively small compared to the carrier. Having this weak signal beside a strong carrier, the detector may be prone to saturation. To avoid this, an adaptive loop may bias the detector. In the loop, an integrator may adjust the bias at the gates such that the DC level of the rectified waveform reaches a reference voltage, $V_{AVG}$. Since this adaptive loop also makes the detector bias robust to any PVT variation, a similar bias loop may be used in reception of downlink data in the external module.

The rectified waveform may then go into a second order RC filter, which may pass the envelop located in vicinity of DC frequency, but may suppress the second harmonic of the carrier frequency. A limiting amplifier may then convert this cleaned envelope waveform into a binary level waveform by slicing it against a threshold voltage, $V_{Th}$. This threshold voltage may be forced to be close to the reference voltage ($V_{Avg}$) by the bias loop. Although FIG. 15 illustrates a particular analog front-end architecture, any of a variety of analog front-end architectures may be utilized as appropriate to the requirements of specific applications in accordance with embodiments of the invention.

Clock and Data Recovery Loop

Figure 16:
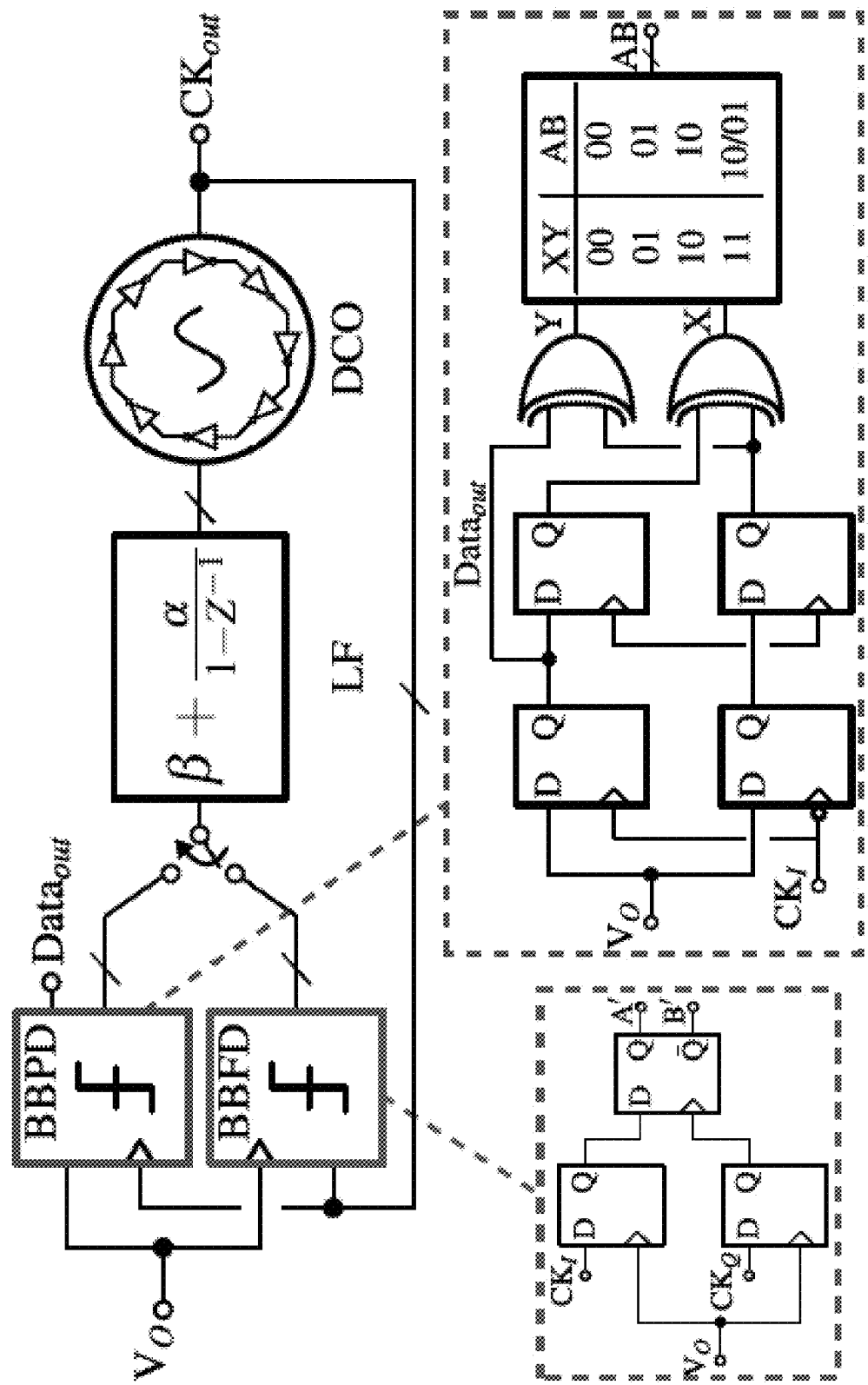
FIG. 16 illustrates a clock and data recovery loop in accordance with an embodiment of the invention.

Although the output waveform of the limiting amplifier looks like binary data, this binary level waveform may need to be re-timed and sampled at the right moments. This data decision may happen in the clock and data recovery loop. A clock and data recovery loop in accordance with an embodiment of the invention is illustrated in FIG. 16. The loop may include a bang-bang phase detector as a one bit time-to-digital converter (TDC), a frequency detector for increasing the acquisition range, an integral and proportional loop filter, and a digital controlled oscillator (DCO).

The bang-bang phase detector may be a modified form of the well-known Alexander phase detector, which can produce synchronous data decisions. This phase detector may also be capable of locking to data waveforms with unbalanced duty cycle (non-50%). These unbalances may appear because of unequal attack and decay times when the load is modulated.

The loop filter can be realized as a digital circuit which implements the transfer function of $\beta+\alpha/(1-Z^{-1})$. The proportional term may be calculated in such a way that it balances the jitter at the input of the loop and the jitter at the output of the DCO. However, the coefficient of the integral term, a, can be chosen for stability. With a nominal input jitter, the loop may be designed to have a phase margin of 50~60 degree. Although FIG. 16 illustrates a particular clock and data recovery loop architecture, any of a variety of clock and data recovery loop architectures may be utilized as appropriate to the requirements of specific applications in accordance with embodiments of the invention.

Figure 17:
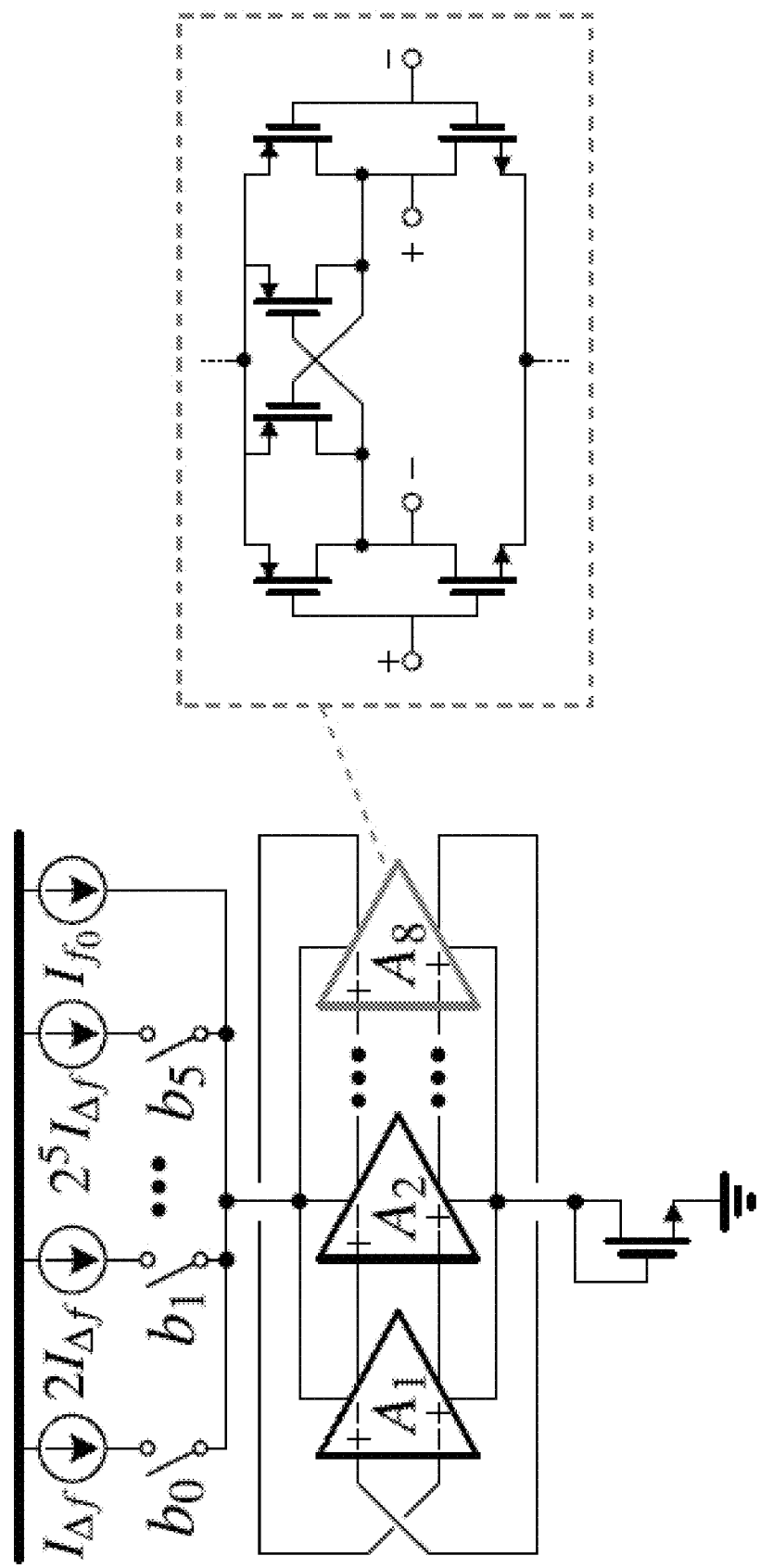
FIG. 17 illustrates a digital controlled oscillator in accordance with an embodiment of the invention.

The digital controlled oscillator can be an eight-stage differential ring oscillator whose frequency is controlled by a 6-bit current DAC. A digital controlled oscillator in accordance with an embodiment of the invention is illustrated in FIG. 17. The number of the bits may be selected so that the quantization noise and the oscillator phase noise contribute equal amounts of jitter at the output of the loop. Each of the delay cells can be realized with two current starved inverters, coupled and boosted with a PMOS cross coupled pair. Although FIG. 17 illustrates a particular digital controlled oscillator architecture, any of a variety of digital controlled oscillator architectures may be utilized as appropriate to the requirements of specific applications in accordance with embodiments of the invention.

Measurements

Figure 18A:
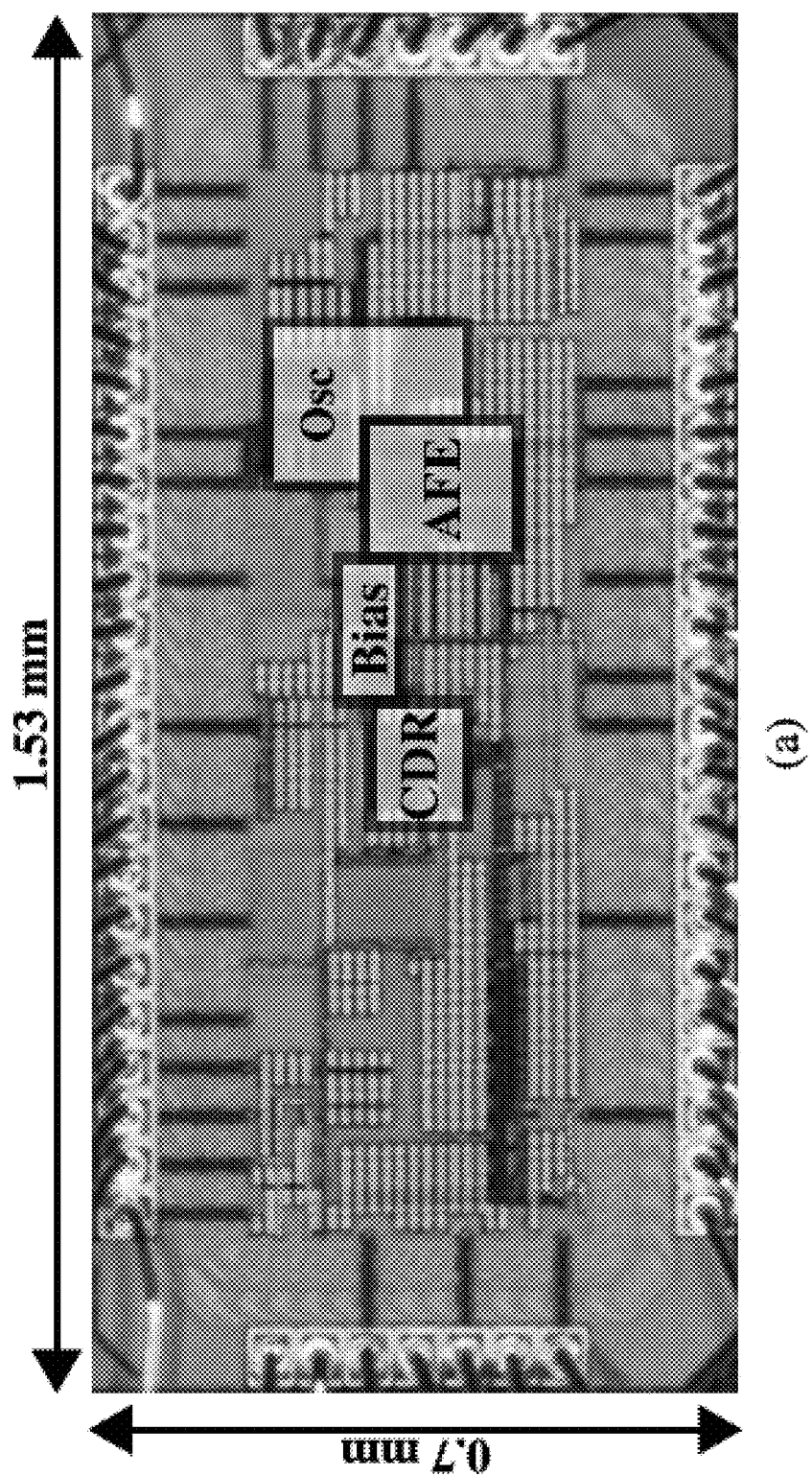
FIG. 18a illustrates an external transceiver chip (TRx) in accordance with an embodiment of the invention.
Figure 18B:
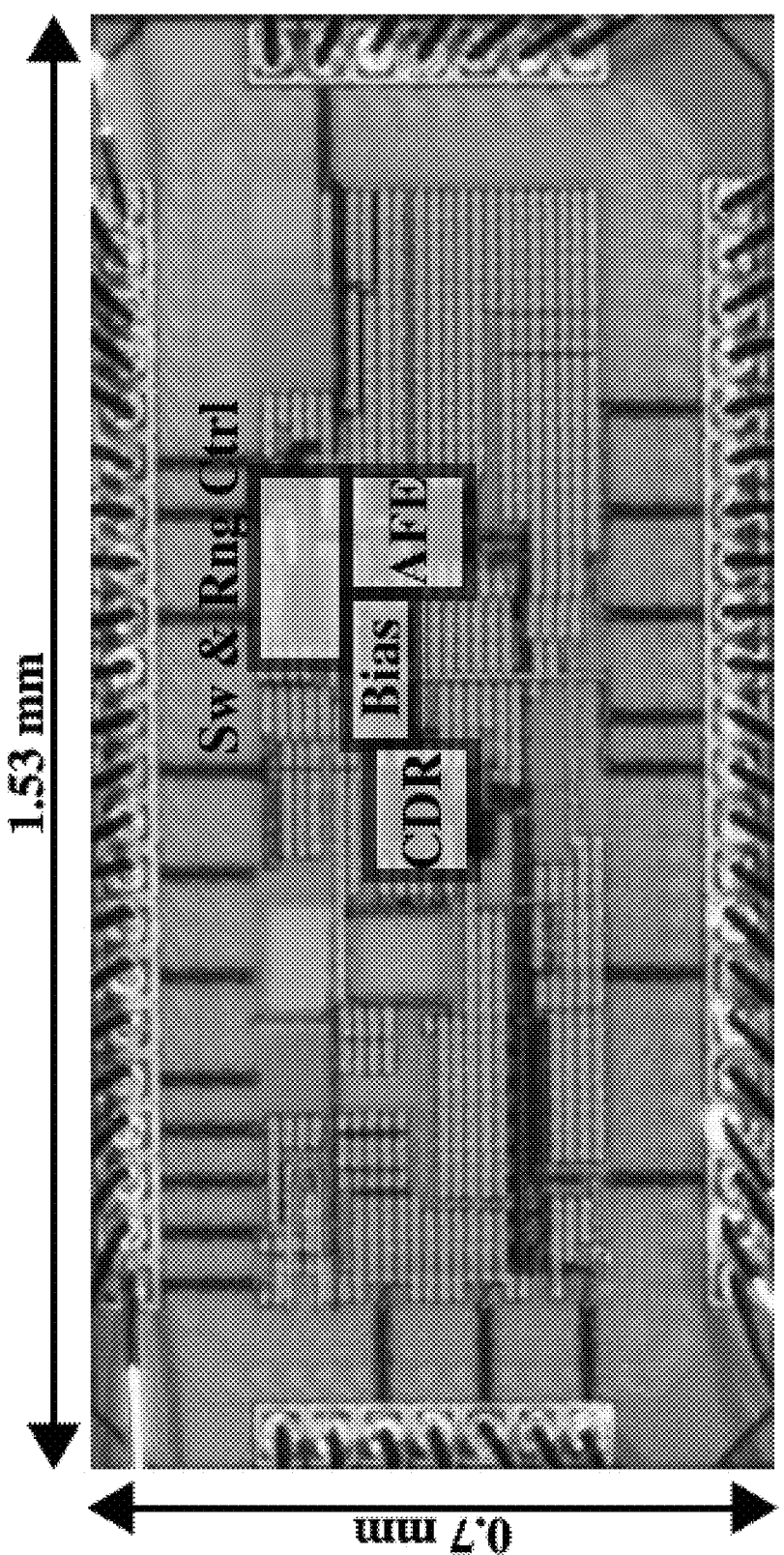
FIG. 18b illustrates an implanted TRx in accordance with an embodiment of the invention.

In several embodiments of the data link system, the transceiver chips can be fabricated in TSMC 40 nm CMOS technology. Photomicrographs of a transceiver chip fabricated in TSMC 40 nm CMOS technology in accordance with an embodiment of the invention is illustrated in FIG. 18, in particular FIG. 18*a* illustrates an external transceiver chip (TRx) and FIG. 18*b* illustrates an implanted TRx in accordance with an embodiment of the invention. The active areas of the implanted and external transceivers can be roughly 0.1 mm2 and 0.12 mm2. For testing, the chips may be housed in 48-pin QFN packages.

In several embodiments of the data link system, the implanted chip may consume only 0.3 µW switching power for transmitting binary data at 4 Mbps in uplink direction. The power dissipation of the implant can be nearly 10 µW, while receiving downlink data at 2 Mbps. The majority of power consumption in the external module may occur in the free running oscillator, which can be approximately 600 µW in uplink and 400 µW in downlink.

Figure 19:
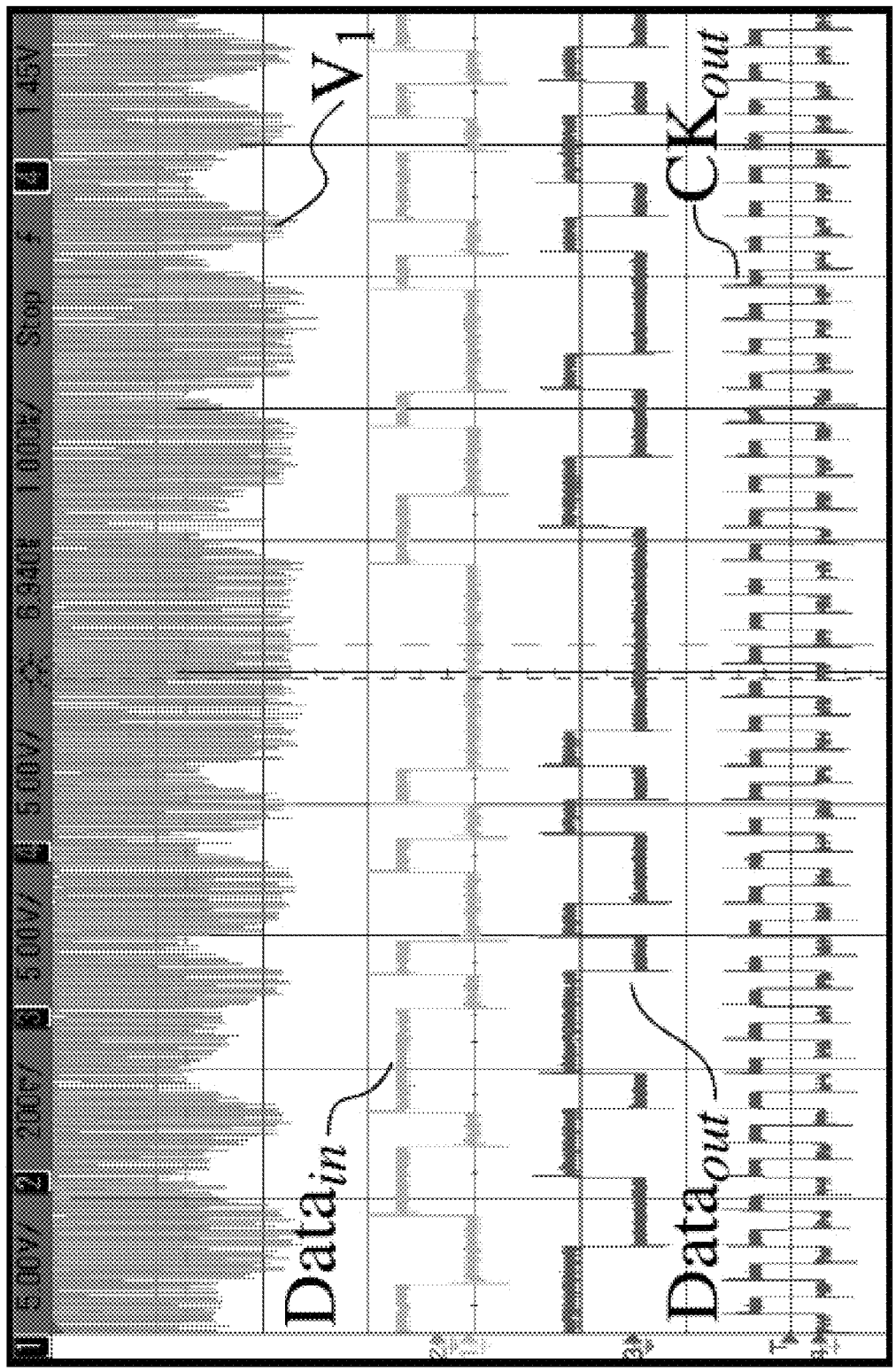
FIG. 19 illustrates measured waveforms in uplink communication: transmitted vs. received.

FIG. 19 illustrates measured waveforms in uplink communication: transmitted vs. received. The waveforms shown in FIG. 19 are the measurement results for uplink at 4 Mpbs. From top to bottom, the first and second waveforms are the free-running oscillator response (on the primary) to switching load on the implant and the binary data which switches the implant load, respectively. The recovered data in the external unit is the third waveform. Comparing the transmitted binary data ($Data_{in}$) and the recovered data ($Data_{out}$), there is a one clock cycle delay, mainly due to the flip-flop delay in the CDR phase detector. The fourth waveform is the reconstructed clock in the CDR.

Figures 20A, 20B:
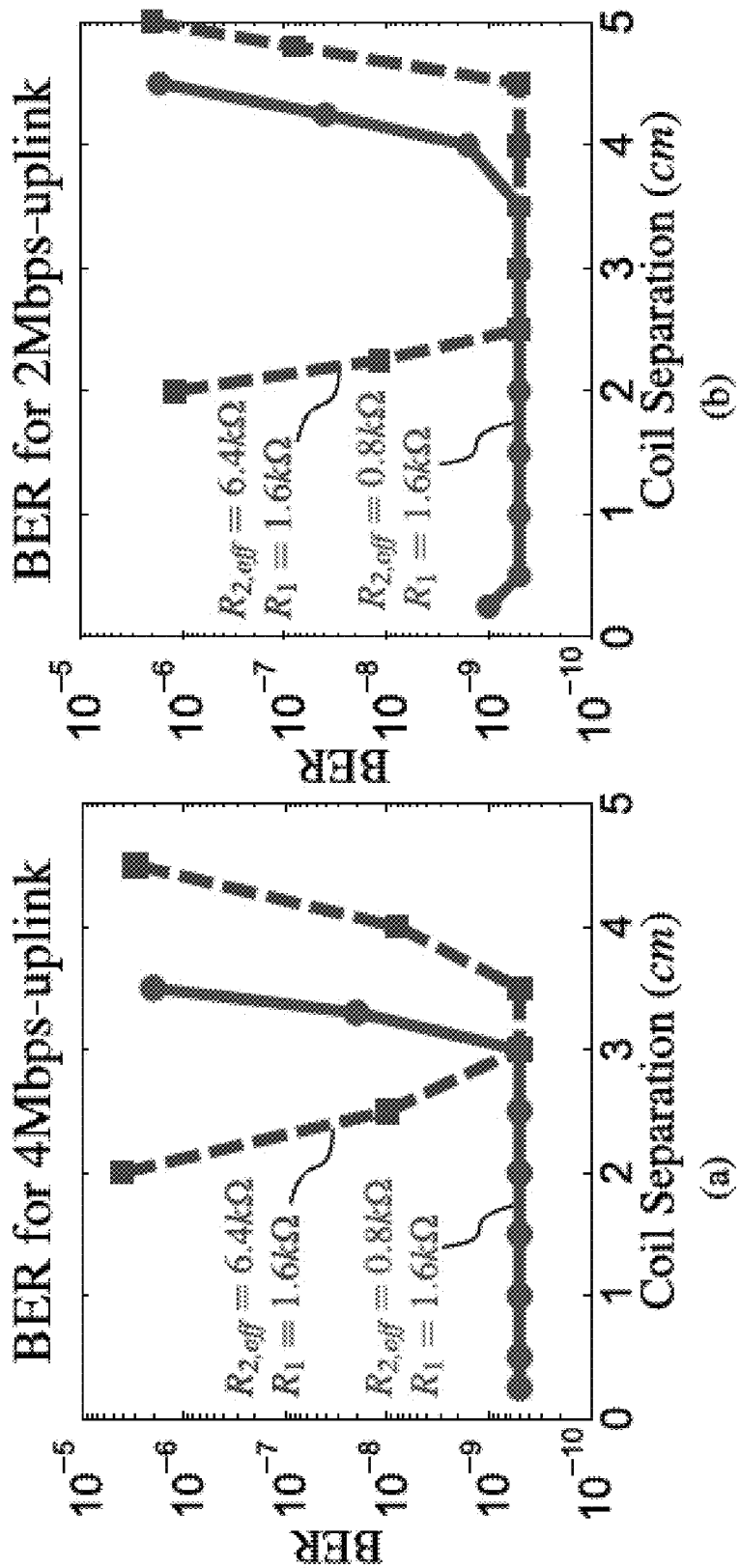
FIG. 20A-B illustrate measured bit error rate (BER) for uplink in accordance with an embodiment of the invention.

To find the range of operation, the bit error rate (BER) of the data link can be measured at different coils distances. For this, a $2^7-1$ pseudo-random generator may be implemented on an FPGA to generate binary data at the transmitter. The received data on the receiver side, then, can be tested in a loop on the FPGA whereby the transmitted and received data has been compared. FIG. 20 illustrates measured bit error rate (BER) for uplink, in particular, FIG. 20a illustrates at a 4 Mbps data rate, and FIG. 20b illustrates at a 2 Mbps data rate. FIG. 20 illustrates measured BER versus coil separation in uplink. At a 4-Mbps data rate, when $R_1=1.6k\Omega$ and $R_2=0.8k$, the coils can be separated by 3 cm~3.5 cm for a respectable BER of $10^{-6}$. By selecting a larger $R_2$ from the resister bank (e.g. $R_2=6.4k\Omega$), this operational range can extend to 4 cm~4.5 cm.

It is worthwhile to note that when $R_2$ is large, for instance $R_2=6.4k\Omega$, the BER can worsen as the coils are brought closer. This is because the modulation index is pinching off, and in this example the null point is located near 2 cm. Also, for a lower data rate of 2 Mbps, the data link is functional up to 5 cm.

In this link, the determining factor in the overall operational range may be the uplink performance, and therefore, over the uplink operational range, the link is fully functional in downlink, as well. This is because, in downlink, the ratio between one and zero levels (corresponding voltages ratio) can be preserved (in this case, the modulation index is 80%). In addition, due to the lower data rate in downlink, $R_2$ can be chosen to be higher compared to uplink, and therefore, the range of downlink can be virtually more than that of uplink.

As it is shown in the table illustrated in FIG. 21, the link can cover the range of 4 cm at 4 Mbps with 3 cm diameter coils. By normalizing this distance ($R_{Max}$) to the coils dimensions ($D_1$ and $D_2$) as follows:

$$R_{Norm} = \frac{R_{Max}}{\sqrt{D_1 \times D_2}} \quad (1)$$

the link may have 2~3 times better normalized range ($R_{Norm}$) compared to the prior art. In addition to this, with comparable data rates, bit error rate and external unit energy consumption per bit, the implanted transceiver can consume much lower energy compared to the state of the art: nearly 2~3 times lower in receive mode and roughly 90 times lower in transmit mode.

Although specific methods and systems for distance-immune inductively-coupled data links are discussed above, many different systems can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:
1. An inductively-coupled data link system comprising:
an external transceiver comprising:
an oscillator configured to generate an oscillator output;
a first inductor;
a first transmitter circuit for transmitting downlink data signals via the first inductor by amplitude modulating the oscillator output;
a first receiving circuit for receiving uplink data signals via the first inductor; and
an implanted transceiver comprising:
a second inductor;
a second receiving circuit for receiving amplitude modulated downlink data signals via the second inductor;
a second transmitter circuit for modulating uplink data signals on an oscillator signal received by the second inductor;
wherein:
the external transceiver and the implanted transceiver are positioned such that an electromagnetic field produced by at least one of the first inductor and the second inductor is inductively coupled to the other inductor; and
the external transceiver further comprises control circuitry that controls the oscillator signal generated by the oscillator as a function of the inductive coupling of the first inductor and the second inductor;
wherein the external transceiver comprises a resistor bank that adjusts channel bandwidth.
2. The data link system of claim 1, wherein the implanted transceiver is configured to modulate the uplink data signals on the oscillator signal received by the second inductor by amplitude modulating the oscillator signal with a data-driven switch that shorts a load on the implanted transceiver.
3. The data link system of claim 2, wherein:
the implanted transceiver comprises a load resistance; and
the load resistance and switch on-resistance of the implanted transceiver prevent inversion of the modulated uplink signal at the external transceiver.
4. The data link system of 3, wherein the load resistance of the implanted transceiver comprises a bank of switched resistors controlled by control circuitry to limit switch on-resistance and prevent inversion of the modulation uplink signal over larger separations of the first and second inductors.
5. The data link system of claim 1, wherein the inductively coupled first inductor is connected directly to the oscillator terminals such that the separation between the first and second inductors tunes the oscillation frequency.
6. The data link system of claim 1, wherein the external transceiver and the implanted transceiver each comprises an analog front-end (AFE) for demodulating a received signal and a clock and data recovery (CDR) loop for providing synchronous data decisions.
7. The data link system of claim 6, wherein the AFE comprises two degenerated common-source MOSFETS with connected drains, wherein the AFE is driven at the device gates by an input differential voltage.
8. The data link system of claim 7, wherein the AFE comprises an adaptive loop to bias a detector, wherein an integrator in the adaptive loop adjusts a bias at the gates such that a DC level of a rectified waveform reaches a reference voltage, $V_{AVG}$.
9. The data link system of claim 8, wherein the rectified waveform goes into a second order RC filter to generate a cleaned envelope waveform, wherein a limiting amplifier converts the cleaned envelope waveform into a binary level waveform by slicing it against a threshold voltage, $V_{TH}$.
10. The data link system of claim 6, wherein the CDR comprises a bang-bang phase detector as a one bit time-to-digital converter (TDC), a frequency detector for increasing acquisition range, an integral and proportional loop filter, and a digital controlled oscillator (DCO).

11. The data link system of claim 10, wherein the bang-bang phase detector is a modified form of an Alexander phase detector that produces synchronous data decisions and that locks to data waveforms with unbalanced duty cycle (non-50%).

12. The data link system of claim 1, wherein the implanted transceiver comprises control circuitry including a resistor bank, where the control circuitry controls the resistance of the resistor bank based upon the inductive coupling of the first inductor and the second inductor.

13. The data link system of claim 1, wherein the level of the oscillator signal is controlled using an amplitude control loop circuit that compares the detected envelope with a DC reference.

14. The data link system of claim 13, wherein the oscillator has a CMOS core and is biased with a binary weighted tail current that is controlled by binary data and an input from the amplitude control loop circuit.

15. The data link system of claim 14, wherein the amplitude control loop circuit comprises an envelope detector for measuring the amplitude of the oscillator, a high gain amplifier for comparing the detected amplitude with a reference voltage, $V_{ref}$, and a digital counter that outputs a binary word controlling the binary-weighted tail current.

16. The data link system of claim 13, wherein the amplitude control loop circuit is only active and adjusts a current source at communication start-up, and during normal operation, the amplitude control loop circuit stops and only the binary data modulates the amplitude of the oscillator.

17. The data link system of claim 16, wherein the external transceiver is configured so that at least a minimal bias current flows continuously through the oscillator during downlink communication.

18. The data link system of claim 17, wherein the external transceiver is configured so that during uplink communication, the current source of the oscillator is kept constant at a maximum while the second transmitter circuit switches its load and thereby modulates the oscillation amplitude.

19. The data link system of claim 1, wherein the implanted transceiver comprises a range control unit that controls a quality factor of a secondary resonator (Q2).

20. An implanted transceiver, comprising:
an inductor;
a receiving circuit for receiving amplitude modulated downlink data signals via the inductor;
a transmitter circuit for modulating uplink data signals on an oscillator signal received by the inductor; and
control circuitry including a resistor bank, where the control circuitry controls the resistance of the resistor bank based upon inductive coupling of the inductor.

21. The implanted transceiver of claim 20, further comprising an analog front-end (AFE) for demodulating a received signal and a clock and data recovery (CDR) loop for providing synchronous data decisions.

22. The implanted transceiver of claim 21, wherein the AFE comprises two degenerated common-source MOSFETS with connected drains, wherein the AFE is driven at the device gates by an input differential voltage.

23. The implanted transceiver of claim 21, wherein the CDR comprises a bang-bang phase detector as a one bit time-to-digital converter (TDC), a frequency detector for increasing acquisition range, an integral and proportional loop filter, and a digital controlled oscillator (DCO).

24. The implanted transceiver of claim 21, wherein the AFE comprises an adaptive loop to bias a detector, wherein an integrator in the adaptive loop adjusts a bias at the gates such that a DC level of a rectified waveform reaches a reference voltage, $V_{AVG}$, wherein the rectified waveform goes into a second order RC filter to generate a cleaned envelope waveform, wherein a limiting amplifier converts the cleaned envelope waveform into a binary level waveform by slicing it against a threshold voltage, $V_{TH}$.

25. An inductively-coupled data link system comprising:
an external transceiver comprising:
an oscillator configured to generate an oscillator output;
a first inductor;
a first transmitter circuit for transmitting downlink data signals via the first inductor by amplitude modulating the oscillator output;
a first receiving circuit for receiving uplink data signals via the first inductor; and
an implanted transceiver comprising:
a second inductor;
a second receiving circuit for receiving amplitude modulated downlink data signals via the second inductor;
a second transmitter circuit for modulating uplink data signals on an oscillator signal received by the second inductor;
wherein:
the external transceiver and the implanted transceiver are positioned such that an electromagnetic field produced by at least one of the first inductor and the second inductor is inductively coupled to the other inductor; and
the external transceiver further comprises control circuitry that controls the oscillator signal generated by the oscillator as a function of the inductive coupling of the first inductor and the second inductor;
wherein the implanted transceiver is configured to modulate the uplink data signals on the oscillator signal received by the second inductor by amplitude modulating the oscillator signal with a data-driven switch that shorts a load on the implanted transceiver;
wherein:
the implanted transceiver comprises a load resistance; and
the load resistance and switch on-resistance of the implanted transceiver prevent inversion of the modulated uplink signal at the external transceiver.

26. An inductively-coupled data link system comprising:
an external transceiver comprising:
an oscillator configured to generate an oscillator output;
a first inductor;
a first transmitter circuit for transmitting downlink data signals via the first inductor by amplitude modulating the oscillator output;
a first receiving circuit for receiving uplink data signals via the first inductor; and
an implanted transceiver comprising:
a second inductor;
a second receiving circuit for receiving amplitude modulated downlink data signals via the second inductor;
a second transmitter circuit for modulating uplink data signals on an oscillator signal received by the second inductor;
wherein:
the external transceiver and the implanted transceiver are positioned such that an electromagnetic field produced by at least one of the first inductor and the second inductor is inductively coupled to the other inductor; and the external transceiver further comprises control circuitry that controls the oscillator signal generated by the oscillator as a function of the inductive coupling of the first inductor and the second inductor;

wherein the external transceiver and the implanted transceiver each comprises an analog front-end (AFE) for demodulating a received signal and a clock and data recovery (CDR) loop for providing synchronous data decisions.

27. An inductively-coupled data link system comprising:
an external transceiver comprising:
   an oscillator configured to generate an oscillator output;
   a first inductor;
   a first transmitter circuit for transmitting downlink data signals via the first inductor by amplitude modulating the oscillator output;
   a first receiving circuit for receiving uplink data signals via the first inductor; and
an implanted transceiver comprising:
   a second inductor;
   a second receiving circuit for receiving amplitude modulated downlink data signals via the second inductor;
   a second transmitter circuit for modulating uplink data signals on an oscillator signal received by the second inductor;
wherein:
   the external transceiver and the implanted transceiver are positioned such that an electromagnetic field produced by at least one of the first inductor and the second inductor is inductively coupled to the other inductor; and
   the external transceiver further comprises control circuitry that controls the oscillator signal generated by the oscillator as a function of the inductive coupling of the first inductor and the second inductor;
wherein the implanted transceiver comprises control circuitry including a resistor bank, where the control circuitry controls the resistance of the resistor bank based upon the inductive coupling of the first inductor and the second inductor.

28. An inductively-coupled data link system comprising:
an external transceiver comprising:
   an oscillator configured to generate an oscillator output;
   a first inductor;
   a first transmitter circuit for transmitting downlink data signals via the first inductor by amplitude modulating the oscillator output;
   a first receiving circuit for receiving uplink data signals via the first inductor; and
an implanted transceiver comprising:
   a second inductor;
   a second receiving circuit for receiving amplitude modulated downlink data signals via the second inductor;
   a second transmitter circuit for modulating uplink data signals on an oscillator signal received by the second inductor;
wherein:
   the external transceiver and the implanted transceiver are positioned such that an electromagnetic field produced by at least one of the first inductor and the second inductor is inductively coupled to the other inductor; and
   the external transceiver further comprises control circuitry that controls the oscillator signal generated by the oscillator as a function of the inductive coupling of the first inductor and the second inductor;
wherein the level of the oscillator signal is controlled using an amplitude control loop circuit that compares the detected envelope with a DC reference.

* * * * *